United States Patent

Cugola et al.

Patent Number: 6,100,289
Date of Patent: *Aug. 8, 2000

[54] INDOLE DERIVATIVES

[75] Inventors: Alfredo Cugola; Romano Di Fabio; Giorgio Pentassuglia, all of Verona, Italy

[73] Assignee: Glaxo Wellcome SpA, Verona, Italy

[ * ] Notice: This patent is subject to a terminal disclaimer.

[21] Appl. No.: 09/374,982

[22] Filed: Aug. 16, 1999

Related U.S. Application Data

[63] Continuation of application No. 09/086,522, May 29, 1998, Pat. No. 5,962,496, which is a continuation of application No. 08/619,510, Mar. 29, 1996, Pat. No. 5,760,059.

[30] Foreign Application Priority Data

Oct. 14, 1993 [GB] United Kingdom .................. 9321221

[51] Int. Cl.⁷ ......................... A61K 31/415; A61K 31/40
[52] U.S. Cl. ............................. 514/404; 514/414
[58] Field of Search .................... 514/323, 313, 514/253, 339, 392, 380, 386, 404, 414

[56] References Cited

U.S. PATENT DOCUMENTS

| | | | |
|---|---|---|---|
| 4,960,786 | 10/1990 | Salituro et al. | 514/419 |
| 5,760,059 | 6/1998 | Cugola et al. | 514/323 |
| 5,962,496 | 10/1999 | Cugola et al. | 514/404 |

FOREIGN PATENT DOCUMENTS

WO 92/16205  10/1992  WIPO.

*Primary Examiner*—Deborah C. Lambkin
*Attorney, Agent, or Firm*—Bacon & Thomas

[57] ABSTRACT

This invention relates to compounds of formula

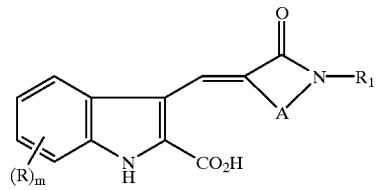

(I)

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ where $R_2$ represents hydroxy, methoxy, amino, alkylamino, or dialkylamino; m is zero or an integer 1 or 2;

$R_1$ represents a cycloalkyl, bridged cycloalkyl, heteroaryl, bridged heterocyclic or optionally substituted phenyl or fused bicyclic carbocyclic group;

A represents a $C_{1-4}$alkylene chain or the chain $(CH_2)_pY(CH_2)_q$ wherein Y is O, S(O)n or $NR_3$ and which chains may be substituted by one or two groups selected from $C_{1-6}$alkyl optionally substituted by hydroxy, amino, alkylamino or dialkylamino, or which chains may be substituted by the group =O;

$R_3$ represents hydrogen, alkyl or a nitrogen protecting group;

n is zero or an integer from 1 to 2;

p is zero or an integer from 1 to 3;

q is zero or an integer from 1 to 3 with the proviso that the sum of p+q is 1, 2 or 3, which are antagonists of excitatory amino acids, to processes for the preparation and to other use in medicine.

12 Claims, No Drawings

INDOLE DERIVATIVES

This application is a continuation of application allowed application Ser. No. 09/086,522 filed May 29, 1998, U.S. Pat. No. 5,962,496, which is a continuation of Ser. No. 08/619,510 filed Mar. 29, 1996, now U.S. Pat. No. 5,760,059.

This invention relates to novel indole derivatives to processes for their preparation, to pharmaceutical compositions containing them and to their use in medicine. In particular it relates to indole derivatives which are potent and specific antagonists of excitatory amino acids.

U.S. Pat. No. 4,960,786 discloses that certain known 2-carboxylic indole derivatives are antagonists of excitatory amino acids. EP-A 0396124 also teaches certain 2-carboxylic indole derivatives as being therapeutically effective in the treatment of CNS disorders resulting from neurotoxic damage or neurodegenerative diseases. Further 3-substituted-2-carboxyindole derivatives which are useful in the treatment of neurodegenerative diseases including cerebrovasular disorders are disclosed in WO92/16205.

We have now found a novel group of 3-substituted-2-carboxyindole derivatives that have a specific antagonist activity at the strychnine insensitive glycine binding site located on the N-methyl-D-aspartate (NMDA) receptor complex.

Accordingly the present invention provides a compound of formula (I)

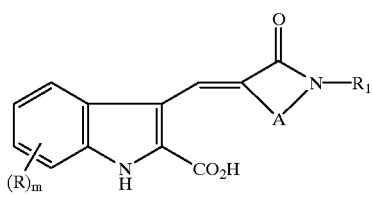

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ wherein $R_2$ represents hydroxy, methoxy, amino, alkylamino, or dialkylamino; m is zero or an integer 1 or 2;

$R_1$ represents a cycloalkyl, bridged cycloalkyl, heteroaryl, bridged heterocyclic or optionally substituted phenyl or fused bicyclic carbocyclic group;

A represents a $C_{1-4}$alkylene chain or the chain $(CH_2)_pY(CH_2)_q$ wherein Y is O, S(O)n or $NR_3$ and which chains may be substituted by one or two groups selected from $C_{1-6}$alkyl optionally substituted by hydroxy, amino, alkylamino or dialkylamino, or which chains may be substituted by the group =O;

$R_3$ represents hydrogen, alkyl or a nitrogen protecting group;

n is zero or an integer from 1 to 2;

p is zero or an integer from 1 to 3;

q is zero or an integer from 1 to 3 with the proviso that the sum of p+q is 1, 2 or 3.

The compounds represented by formula (I) can exist in more than one isomeric form and all possible isomers are included in formula (I) unless otherwise specified. Thus in compounds of formula (I) the exocyclic double bond can exist in the cis or trans configuration and the invention includes both isomers and mixtures thereof.

For use in medicine the salts of the compound of formula (I) will be physiologically acceptable thereof. Other salts however may be useful in the preparation of the compounds of formula (I) or physiologically acceptable salts thereof. Therefore unless otherwise stated references to salts includes both physiologically acceptable salts and non-physiologically acceptable salts of compounds of formula (I).

Suitable physiologically acceptable salts of compounds of the invention include base addition salts and where appropriate acid addition salts. Suitable physiologically acceptable base addition salts of compounds of formula (I) include alkali metal or alkaline metal salts such as sodium, potassium, calcium, and magnesium salts, and ammonium salts, formed with amino acids (e.g. lysine and arginine) and organic bases (e.g. procaine, phenylbenzylamine, ethanolamine diethanolamine and N-methyl glucosamine).

Suitable acid addition salts may be formed with organic acid and inorganic acids e.g. hydrochloric acid.

The compounds of formula (I) and or salts thereof may form solvates (e.g. hydrates) and the invention includes all such solvates.

It will be appreciated that the compound of formula (I) may be produced in vivo by metabolism of a suitable prodrug. Such prodrugs may be for example physiologically acceptable metabolically labile esters of compounds of the general formula (I). These may be formed by esterification of the carboxylic acid group in the parent compound of general formula (I) with where appropriate prior protection of any other reactive groups present in the molecule followed by deprotection if required. Examples of such metabolically labile esters include $C_{1-4}$alkyl esters e.g. methyl ethyl or t-butyl esters esters, $C_{3-6}$alkenyl esters e.g. allyl substituted or unsubstituted aminoalkyl esters (e.g. aminoethyl, 2-(N,N-diethylamino) ethyl, or 2-(4-morpholino)ethyl esters or acyloxyalkyl esters such as, acyloxymethyl or 1-acyloxyethyl e.g. pivaloyloxymethyl, 1-pivaloyloxyethyl, acetoxymethyl, 1-acetoxyethyl,1-(1-methoxy-1-methyl)ethylcarbonyloxyethyl, 1-benzoyloxyethyl, isopropoxycarbonyloxymethyl, 1-isopropoxycarbonyloxyethyl, cyclohexylcarbonyloxymethyl, 1-cyclohexylcarbonyloxyethyl ester, cyclohexyloxycarbonyloxymethyl, 1-cyclohexyloxycarbonyloxyethyl, 1-(4-tetrahydropyranyloxy)carbonyloxyethyl or 1-(4-tetrahydropyranyl)carbonyloxyethyl.

Preferred metabolically labile esters of compounds of formula (I) include $C_{1-4}$alkyl esters more particular methyl or ethyl, aminoalkyl esters more particular 2-(4'-morpholino)ethyl, or acyloxyalkyl esters e.g. acetoxymethyl, pivaloyloxymethyl, 1-cyclohexyloxycarbonyloxyethyl or 1-(4-tetrahydropyranyloxycarbonyloxy)ethyl.

The group R may be at any of the four possible positions on the fused benzene ring and when m is 2 the two R groups may be the same or different.

Unless otherwise specified the term alkyl as used herein as a group or part of a group refers to a straight or branched chain alkyl group containing from 1 to 4 carbon atom examples of such groups include methyl, ethyl propyl, isopropyl, n-butyl, isobutyl, secondary butyl or tertiary butyl.

The term halogen refers to a fluorine, chlorine bromine or iodine atom.

The term cycloalkyl refers to a $C_{5-7}$cycloalkyl group which may optionally be substituted by 1 or 2 $C_{1-4}$alkyl groups, e.g. cyclopentyl, cyclohexyl, cycloheptyl or 2-methylcyclohexyl.

The term bridged cycloalkyl refers to a group containing from 7 to 10 carbon atoms and which is saturated or contains a single double bond. Examples of suitable bridged cycloalkyl groups include adamantyl, such as 1-adamantyl or 2-adamantyl, noradamantyl, bicyclo(2,2,1)heptanyl such as 2-norbomanyl, or bicyclo (2,2,1) heptenyl such as 5-norbomenyl.

The term heteroaryl refers to a 5 or 6 membered heteroaryl group in which the 5-membered heteroaryl group contains 1 or 2 heteroatoms selected from oxygen, sulphur or nitrogen and 6-membered heteroaryl group containing 1 or 2 nitrogen atoms, which heteroaryl groups may be optionally fused to a benzene ring. Examples of suitable heteroaryl groups include furanyl, thiophenyl, imidazolyl, thiazolyl, oxazolyl, pyridinyl, pyrimidinyl and quinolinyl.

The term bridged heterocyclic refers to a bridged heterocyclic ring system containing from 7 to 10 ring members selected from carbon, oxygen or nitrogen and which bridged heterocyclic system is saturated or contains a single double bond. Preferably the bridged heterocyclic group contains a single heteroatom selected from oxygen or nitrogen. Examples of suitable bridged heterocyclic groups include 7-oxa-bicyclo (2,2,1) heptanyl, 7-oxa-bicyclo (2,2,1) heptenyl, 7-aza-bicyclo (2,2,1) heptanyl, 7-aza-bicyclo (2,2, 1) heptenyl or 1-azabicyclo (2,2,2) octanyl such as 3-quinuclidinyl.

The term fused bicyclic carbocyclic group refers to a 5,6/6,5 or 6,6 bicyclic carbocyclic ring system containing 9 or 10 carbon atoms and which may be saturated or unsaturated. Examples of such groups include naphthyl, tetrahydronaphthyl, decahydronaphthyl, indenyl or indanyl.

When the group $R_1$ is a substituted phenyl or fused bicyclic carbocyclic group this refers to a group which is substituted by 1 to 3 groups selected from halogen, alkyl, alkoxy, amino, alkylamino, dialkylamino, $C_{1-6}$alkanoylamino, ureido, alkylsulphonylamino, hydroxy, trifluoromethyl, trifluoromethoxy, nitro, cyano, $SO_2R_2$ or $COR_2$ wherein $R_2$ represents hydroxy, methoxy, amino, alkylamino or dialkylamino.

When A is an optionally substituted $C_{1-4}$alkylene chain this may be for example methylene, ethylene, propylene, butylene or $CH_2CO$. When A is the chain $(CH_2)_p Y (CH_2)_q$ this may be for example $CH_2OCH_2$, $CH_2NR_3CH_2$, $CH_2NH$, NHCO, $CH_2NCH_3$, $CH_2CH_2NH$, or $CH_2O$.

When $R_3$ is a nitrogen protecting group this may be for example optionally substituted benzyl, alkoxycarbonyl group e.g. t-butoxycarbonyl, aralkyloxycarbonyl, trimethylsilylethoxymethyl or arylsulphonyl e.g. phenylsulphonyl.

A preferred class of compounds of formula (I) are those wherein m is 1 or 2 and within this class those wherein R is at the 4 and/or 6 position are particularly preferred.

Examples of suitable R groups include chloro-, bromo-, iodo-, methyl or ethyl. More preferably R is a chloro group.

The group $R_3$ is conveniently hydrogen or C1–4alkyl e.g. methyl.

Conveniently the chain A is a group selected from $C_{2-3}$alkylene optionally substituted by the group =O, e.g. $—(CH_2)_2—$, $—CH_2CO—$ or $—(CH_2)_3—$ or $—(CH_2)_p Y (CH_2)_q—$ wherein p is 1 or 2, q is zero and Y is NH, $NCH_3$ or 0 e.g. $—CH_2NH—CH_2NCH_3—(CH_2)_2NH—$ or $—CH_2O—$ or p is zero, Y is NH, q is 1 or 2 and the group $(CH_2)_q$ is substituted by the group =0 e.g. $—NHCO—$.

A preferred class of compounds of formula (I) include these wherein A is a chain selected from $—(CH_2)_2—$, $—(CH_2)_3—$, $—CH_2CO—$, $—CH_2NH—$, $—CH_2NCH_3$, $—CH_2O—$ or NHCO. Within this class those compounds wherein A is $(CH_2)_2—$ or more particularly $—CH_2NH—$ are especially preferred.

Conveniently the group $R_1$ is a group selected from optionally substituted phenyl, naphthyl e.g. 1-naphthyl, pyridyl e.g. 2-pyridyl, quinolinyl e.g. 2-quinolinyl, cyclohexyl or adamantyl e.g. 2-adamantyl.

When $R_1$ is an optionally substituted phenyl group this is conveniently phenyl or phenyl substituted by amino, acetylamino, methanesulphonylamino or ureido which substituent is in the meta or more preferably the para position.

A further preferred class or compounds of formula (I) are those wherein $R_1$ represents phenyl, or phenyl substituted by amino, acetylamino, methanesulphonylamino or ureido. Within this class those wherein $R_1$ is phenyl are particularly preferred.

Compounds wherein $R_1$ is optionally substituted phenyl, or 1-naphthyl represent yet a further preferred class of compounds of formula (I).

Compounds of formula (I) wherein the exocyclic double bond is in the trans (E) configuration represent yet a further preferred class of compounds of the invention.

A preferred group of compounds of formula (I) are those wherein m is 2 and R is chlorine in the 4 and 6 positions. A is a chain selected from $—(CH_2)_2—$, $—(CH_2)_3—$, $—CH_2CO—$, $—CH_2NH—$, $CH_2NCH_3—$, $—(CH_2)_2NH—$, $—CH_2O—$; or $—NHCO—$, and $R_1$ is a group selected from optionally substituted phenyl.

A further preferred group of compounds of formula (I) are those wherein m is 2 and R is chlorine in the 4 and 6 positions, A is $CH_2NH$ and $R_1$ is optionally substituted phenyl, 2-pyridyl, 2-quinolinyl, 1-naphthyl, cyclohexyl or 2-adamantyl. Within this group particularly preferred compounds are the trans (E) isomers thereof. More particularly the compounds wherein $R_1$ is optionally substituted phenyl e.g. phenyl or phenyl substituted by amino, are especially preferred.

A particularly preferred compound of the invention is (E) 4,6-dichloro-3-(5-oxo-1-phenyl-pyrazolidin-4-ylidenemethyl)-1H-indole-2-carboxylic acid and physiologically acceptable salts thereof e.g. sodium or potassium salts or metabolically labile esters thereof.

Further preferred compounds include
(E) -4,6-dichloro-3-(2-oxo-1-phenyl-pyrrolidin-3-yl idenemethyl)-1H-indole-2-carboxylic acid;
(E)-4,6-dichloro-3-(2-oxo-1-phenyl-piperidin-3-ylidenemethyl)-1H-indole-2-carboxylic acid;
(E) 4,6-dichloro-3-[(5-oxo-1-(4-aminophenyl)pyrazolidin-4-ylidenemethyl]-1H-indole-2-carboxylic acid;
(Z) 4,6-Dichloro-3-(2,5-dioxo-1-phenyl-imidazolidin-4-ylidenemethyl)-1H-indole-2-carboxylic acid;
(E) 4,6-Dichloro-3-(2,5-dioxo-1-phenyl-imidazolidin-4-ylidenemethyl)-1H-indole-2-carboxylic acid;
4,6-Dichloro-3-[5-oxo-1-(4-acetylamino-phenyl)-pyrazolidin-4-ylidenemethyl]-1H-indole-2-carboxylic acid;
4,6-Dichloro-3-[5-oxo-1-(4-ureido-phenyl)-pyrazolidin-4-ylidenemethyl]-1H-indole-2-carboxylic acid;
4,6-Dichloro-3-[1-(4-methylsulfamidophenyl)-5-oxo-pyrazolidin-4-ylidenemethyl]-1H-indole-2-carboxylic acid;
4,6-Dichloro-3-(3-oxo-2-phenyl-isoxazolidin-4-ylidene methyl)-1H-indole-2-carboxylic acid;
(E) 4,6-dichloro-3-[(5-oxo-1-(3-aminophenyl)pyrazolidin-4-ylidenemethyl]-1H-indole-2-carboxylic acid;
(E) 4,6-dichloro-3-(2,5-dioxo-1-phenyl-pyrrolidin-3-ylidenemethyl)-1H-indole-2-carboxylic acid;

(E) 4,6-dichloro-3-[(5-oxo-1-(1-naphthyl)pyrazolidin-4-ylidenemethyl]-1H-indole-2-carboxylic acid;
and physiologically acceptable salts thereof e.g. sodium or potassium salts or metabolically labile esters thereof.

The compounds of formula (I) and or physiologically acceptable salts thereof are excitatory amino acid antagonists. More particularly they are potent antagonists at the strychnine insensitive glycine binding site associated with the NMDA receptor complex. As such they are potent antagonists of the NMDA receptor complex. Moreover the compounds of the invention exhibit an advantageous profile of activity including good bioavaibility. These compounds are therefore useful in the treatment or prevention of neurotoxic damage or neurodegenerative diseases. Thus the compounds are useful for the treatment of neurotoxic injury which follows cerebral stroke, thromboembolic stroke, hemorrhagic stroke, cerebral ischemia, cerebral vasospam, hypoglycemia, anaesia, hypoxia, anoxia, perinatal asphyxia cardiac arrest. The compounds are useful in the treatment of chronic neurodegenerative diseases such as: Huntingdon's disease, Alzheimer's senile dementia, amyotrophic lateral sclerosis, Glutaric Acidaemia type, multi-infarct dementia, status epilecticus, contusive injuries (e.g. spinal cord injury and head injury), viral infection induced neurodengeration, (e.g. AIDS, encephalopaties), Down syndrome, epilepsy, schizophrenia, depression, anxiety, pain, neurogenic bladder, irritative bladder disturbances, drug dependency, including withdrawal symptoms from alcohol, cocaine, opiates, nicotine, benzodiazepine, and emesis.

The potent and selective action of the compound of the invention at the strychnine- insensitive glycine binding site present on the NMDA receptor complex may be readily determined using conventional test procedures. Thus the ability to bind at the strychnine insensitive glycine binding site was determined using the procedure of Kishimoto H et al. J Neurochem 1981, 37 1015–1024. The selectivity of the action of compounds of the invention for the strychnine insensitive glycine site was confirmed in studies at other ionotropic known excitatory amino acid receptors. Thus compound of the invention were found to show little or no affinity for the kainic acid (kainate) receptor, a-amino-3-hydroxy-5-methyl-4-isoxazole-proprionic acid (AMPA) receptor or at the NMDA binding site.

Compounds of the invention have also been found to inhibit NMDA induced convulsions in mice using the procedure Chiamulera C et al. Psychophamacology (1990) 102, 551–552.

The neuroprotective activity of compounds of the invention may be demonstrated in the middle cerebral artery occlusion preparation in mice, using the procedure described by Chiamulera C et al. European Journal of Pharmacology 216 (1992) 335–336.

The invention therefore provides for the use of a compound of formula (I) and or physiologically acceptable salt or metabolically labile ester thereof for use in therapy and in particular use as medicine for antagonising the effects of excitatory amino acids upon the NMDA receptor complex.

The invention also provides for the use of a compound of formula (I) and/or a physiologically acceptable salt or metabolically labile ester thereof for the manufacture of a medicament for antagonising the effects of excitatory amino acids upon the NMDA receptor complex.

According to a further aspect the invention also provides for a method for antagonising the effects of excitatory amino acids upon the NMDA receptor complex, comprising administering to a patient in need thereof an antagonistic amount of a compound of formula (I) and/or a physiologically acceptable salt or metabolically labile ester thereof.

It will be appreciated by those skilled in the art that reference herein to treatment extends to prophylaxis as well as the treatment of established diseases or symptoms.

It will further be appreciated that the amount of a compound of the invention required for use in treatment will vary with the nature of the condition being treated the route of administration and the age and the condition of the patient and will be ultimately at the discretion of the attendant physician. In general however doses employed for adult human treatment will typically be in the range of 2 to 800 mg per day, dependent upon the route of administration.

Thus for parenteral administration a daily dose will typically be in the range 20–100 mg preferably 60–80 mg per day. For oral administration a daily dose will typically be within the range 200–800 mg e.g. 400–600 mg per day.

The desired dose may conveniently be presented in a single dose or as divided doses administered at appropriate intervals, for example as two, three, four or more sub-doses per day.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable salt or metabilically labile ester thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

The compositions of the invention include those in a form especially formulated for oral, buccal, parenteral, inhalation or insufflation, implant, or rectal administration. Parenteral administration is preferred.

Tablets and capsules for oral administration may contain conventional excipients such as binding agents, for example, syrup, accacia, gelatin, sorbitol, tragacanth, mucilage of starch or polyvinylpyrrolidone; fillers, for example, lactose, sugar, microcrystalline cellulose, maize-starch, calcium phosphate or sorbitol; lubricants, for example, magnesium stearate, stearic acid, talc, polyethylene glycol or silica; disintegrants, for example, potato starch or sodium starch glycollate, or wetting agents such as sodium lauryl sulphate. The tablets may be coated according to methods well known in the art. Oral liquid preparations may be in the form of, for example, aqueous or oily suspensions, solutions emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example, almond oil, fractionated coconut oil, oily esters, propylene glycol or ethyl alcohol; solubilizers such as surfactants for example polysorbates or other agents such as cyclodextrins; and preservatives, for example, methyl or propyl p- hydroxybenzoates or ascorbic acid. The compositions may also be formulated as suppositories, e.g. containing conventional suppository bases such as cocoa butter or other glycerides.

For buccal administration the composition may take the form of tablets or lozenges formulated in conventional manner.

The composition according to the invention may be formulated for parenteral administration by injection or continuous infusion. Formulations for injection may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs, with the use of a suitable propellant, such as dichlorodifluoromethane, tirchlorofluoromethane, dichlorotetrafluoroethane, carbon dioxide or other suitable propellant, such as dichlorodiffluoromethane, trichlorofluoromethane, dichloro-tetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable carrier such as lactose or starch. The powder composition may be presented in unit dosage form in for example capsules or cartridges of e.g. gelatin, or blister packs from which the powder may be administered with the aid of an inhaler or insufflator.

The composition according to the invention may also be formulated as a depot preparation. Such long acting formulations may be administered by implantation (for example subcutaneously or intramuscularly) or by intramuscular injection. Thus for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups R, $R_1$, and $R_2$, m and A are as defined for the compounds of formula (I) unless otherwise stated.

Compounds of formula (I) wherein A has the meanings defined above with the proviso that A is not —NHCO— may be prepared by reaction of the aldehyde (II) (wherein R has the meanings defined above in formula (I) or is protected derivative thereof, $R_4$ is a carboxyl protecting group and $R_5$ is a nitrogen protecting group),

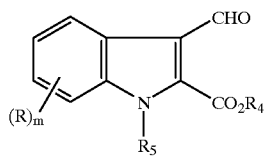

(II)

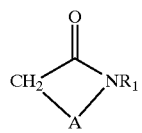

(III)

with the cyclic amide (III) (wherein $R_1$ and A have the meanings defined above in formula (I) or are protected derivatives thereof, with the proviso that A is not the group NHCO—) in the presence of a suitable base and if necessary or desired subjecting the resulting compound to one or more of the following operations.

a) removal of one or more protecting groups
b) isolation of the compound as a salt thereof
c) conversion of a compound of formula (I) or a salt thereof into a metabolically labile ester
d) conversion of a compound of formula (I) into a physiologically acceptabe salt thereof.

In one embodiment of this process the aldehyde (II) is reacted with the cyclic amide (III) in the presence of a base such as t-butyl lithium, lithium diisopropylamide, or lithium bis(trimethylsilyl)amine in an aprotic solvent such as tetrahydrofuran. The reaction is initially carried out at a temperature around −78° but is then allowed to rise to 0° to 30° C.

The initial product of this reaction will depend upon the nature of the protecting groups $R_4$ and $R_5$ since some of these may be cleaved under the reaction conditions. Examples of such groups include those wherein $R_4$ is methyl or ethyl and or $R_5$ is alkoxycarbonyl e.g. t-butoxycarbonyl.

In the event that the reaction is carried out using an indole of formula (II) wherein the carboxyl protecting group $R_4$ is cleaved e.g. $R_4$ is ethyl but the nitrogen protecting group $R_5$ is not, e.g. trimethylsilyl-ethoxymethyl the resultant carboxylic acid IV

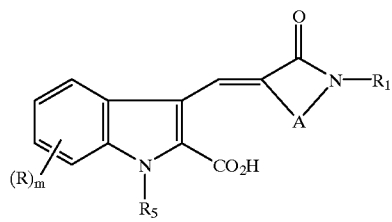

(IV)

may be converted into a compound of formula (I) by removal of the nitrogen protecting group $R_5$. Alternatively the carboxylic acid (IV) may be converted into the corresponding methyl ester (V) by reaction with diazomethane. For this rection trimethylsilyldiazomethane is a convenient source of diazomethane and the reaction may be carried out in a suitable solvent such as a halohydrocarbon e.g. dichloromethane.

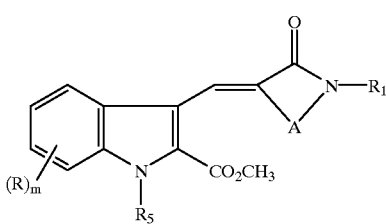

(V)

The compound of formula (V) may be converted into a compound of formula (I) by removal of the nitrogen protecting group $R_5$ using conventional means followed where desired or necessary by hydrolysis of the methyl ester.

In a second embodiment of the process the aldehyde (II) is reacted with the cyclic amide (III) in the presence of a base such as butyl lithium, lithium diisopropylamide, or lithium bis(trimethylsilyl)amide in an aprotic solvent such as tetrahydrofuran and at a temperature of around −78°. Reaction of the resultant secondary alcohol (VI)

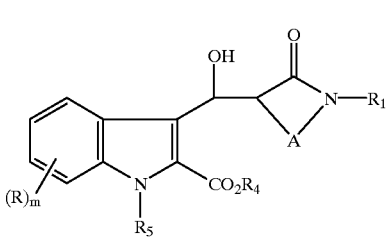

(VI)

with hydrochloric acid and with heating in a solvent such as ethanol yields the olefine (VII)

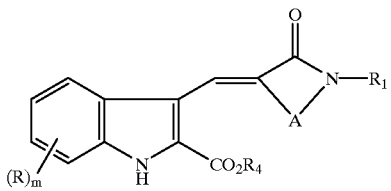

(VII)

The ester (VII) may be converted into a compound of formula (I) by removal of the carboxyl protecting group $R_4$ using conventional procedures.

In a modification of this process the secondary alcohol (VI) may be converted into a reactive leaving group such as a sulphonate ester e.g. p-toluenesulphonate or methanesulphonate followed by treatment with an appropriate base such as lithium diisopropylamide or sodium ethoxide. The resultant olefin may then be converted into a compound of the formula (I) by removal of the nitrogen protecting group $R_5$ and where necessary or desired the carboxyl protecting group $R_4$.

Suitable carboxyl protecting groups $R_4$ for use in these reactions include allyl, alkyl, trichloroalkyl, trialkylsilylalkyl or arylmethyl groups such as benzyl, nitrobenzyl or trityl.

Suitable nitrogen protecting groups $R_5$ include alkoxycarbonyl e.g. t-butoxycarbonyl, arylsulphonyl e.g. phenylsulphonyl or 2-trimethylsilylethoxymethyl.

The carboxyl protecting group $R_4$ may be removed by conventional procedures known for removing such groups.

Thus compounds when $R_4$ is an alkyl group, this may be removed by hydrolysis using an alkali metal hydroxide e.g. lithium hydroxide or sodium hydroxide in a solvent such as an alkanol e.g. ethanol or isopropanol, followed where desired or necessary by that addition of a suitable acid e.g. hydrochloric acid or trifluoroacetic acid to give the corresponding free carboxylic acid.

When $R_4$ is an allyl group this may be removed by treatment with an allyl receptor such as 5,5-dimethyl-1,3-cyclohexandione in the presence of tetrakis (triphenylphosphine) palladium.

Alternatively compounds wherein $R_4$ is an alkyl or benzyl group may be converted into the corresponding carboxylic acid by reaction with trimethylsilyl iodide in a solvent such as acetonitrile and with heating.

In any of the above reactions the nitrogen protecting group may be removed by conventional procedures known for removing such groups, for example by acid or base hydrolysis. Thus when $R_5$ is alkoxycarbonyl e.g. t-butoxycarbonyl may be removed by alkaline hydrolysis using for example lithium hydroxide in a suitable solvent such as tetrahydrofuran or an alkanol e.g. isopropanol or acid hydrolysis e.g. with formic acid, trifluoroacetic acid or hydrogen chloride in a solvent. When $R_5$ is a trimethylsilylethoxymethyl group this may be removed by acid hydrolysis using hydrochloric acid or hydrogen chloride in a solvent such as an alkanol e.g. ethanol.

Physiologically acceptable salts of compounds of formula (I) may be prepared by treating the corresponding acid with an appropriate base in a suitable solvent. For example alkali and alkaline metal salts may be prepared from an alkali or alkaline metal hydroxide, or the corresponding carbonate or bicarbonate salts thereof. Alternatively alkali or alkaline metal salts may be prepared by direct hydrolysis of carboxyl protected derivative of compound of formula (I) with the appropriate alkali or alkaline metal hydroxide.

When the compound of formula (I) contains a basic centre acid addition salts may be prepared by reaction of the base with the appropriate acid and optionally in a solvent. Alternatively the acid addition salt may be obtained by direct hydrolysis of a carboxyl protected and or nitrogen protected derivative thereof by reaction with the appropriate acid.

Metabolically labile esters of compounds of formula (I) may be prepared by esterification of the carboxylic acid group or a salt thereof or by trans esterification using conventional procedures. Thus for example acyloxyalkyl esters may be prepared by reacting the free carboxylic acid or a salt thereof with the appropriate acyloxylalkyl halide in a suitable solvent such as dimethylformamide. For the esterification of the free carboxyl group this reaction is preferably carried out in the presence of a quaternary ammonium halide such as tetrabutylammonium chloride or benzyltriethylammonium chloride.

Aminoalkyl esters may be prepared by transesterfication of a corresponding alkyl ester e.g. methyl or ethyl ester by reaction with the corresponding aminoalkanol at an elevated temperature e.g. 50–150°.

For the reaction of the aldehyde (II) with the cyclic amide (III) it may be necessary or desirable to carry out the reaction using protected derivatives thereof. For example when one or both compounds contain a primary or secondary amino group, or a hydroxyl or carboxyl group. These groups may be protected in a conventional manner and the protecting groups removed using conventional procedures as and when required.

Thus when the group R is amino or alkylamino, and or $R_1$ contains an amino or alkylamino substituent and or the group A contains a basic —NH— group then it is desirable that each such basic nitrogen atom is protected e.g. as a t-butoxycarbonyl derivative thereof. The nitrogen protecting group may then be removed by conventional means; for example reaction with trifluoroacetic acid in a suitable solvent e.g. dichloromethane, or hydrogen chloride in a solvent such as an alkanol.

Any hydroxy or carboxyl group may be conveniently protected as an ester thereof such as a t-butoxycarbonyl derivative of the hydroxy group or an alkyl or allyl ester of the carboxyl group e.g. t-butyl or allyl ester thereof.

Compounds of formula (I) wherein A is the chain NHCO may be prepared by reaction of the aldehyde (II) or a protected derivative thereof with the glycine derivative (VIII)

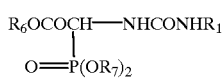
(VIII)

wherein $R_1$ is a group as defined in formula (I) or a protected derivative thereof and $R_6$ and $R_7$ independently represent $C_{1-4}$alkyl. The reaction is carried out on the presence of a base such as 1,8-diazabicyclo [5.4.0] undec-7-ene in an aprotic solvent such as ether e.g. tetrahydrofuran followed by removal of the protecting groups $R_4$ and $R_5$ together with any other protecting group present.

Compounds of formula (I) wherein A is the group $CH_2CO$ may be prepared by reaction of the aldehyde (II) with the phosphorane derivative (IX) wherein $R_1$ has the meanings defined in formula 1 or is a protected derivative thereof.

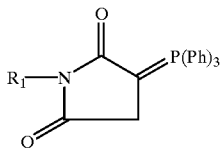
(IX)

The reaction is preferably carried out with heating in a suitable solvent e.g. a hydrocarbon such as toluene, followed by removal of the protecting groups $R_4$ and $R_5$, in a conventional manner.

Compounds of formula (I) wherein the exocyclic bond is in the cis configuration may be prepared isomerisation of the corresponding transisomer or a protected derivative thereof, followed by removal of any protecting group. The isomerisation reaction is conveniently carried out by irradiating a solution of the trans isomer in a suitable solvent such as acetonitrile with UV light e.g. from a mercury lamp.

Compounds of formula (II) wherein $R_4$ is a carboxyl protecting group, and $R_5$ is a nitrogen protecting group may be prepared by treating the corresponding indole (X).

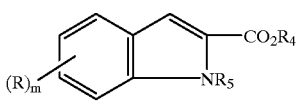
(X)

above with N-methylformanilide and phosphorous oxychloride in a solvent such as 1,2-dichloroethane.

The indoles of formula (X) are either known compounds or may be prepared by analogous methods to these described for the known compounds.

The cyclic amides of formula (III) are either known compounds or may be prepared using methods analogous to those described for known compounds e.g. Manhas and Jeng J. Org. Chem. 1967, 32 1246–1248, or Hargis D C and Shubkin R L Tetrahedron Letters vol 31 No 21 pp 2991–4, 1990.

Thus compounds of formula (III) wherein A is the group $(CH_2)_p$ $NR_8$ wherein p is 1 or 2 and $R_8$ is a protecting group may be prepared by reaction of protected hydrazine $R_1NH$ $NHR_8$ with the haloacyl halide (XI).

$$Z(CH_2)_rCOZ^1 \qquad (XI)$$

wherein Z and $Z^1$ are independently a halogen atoms e.g. chlorine bromine or iodine and r is 2 or 3. The reaction is conveniently carried out in the presence of a base such as an alkali metal carbonate and in a polar solvent such as N,N-dimethylformamide. A suitable protecting group $R_8$ for use in this reaction is t-butyloxycarbonyl group. If required this protecting group may be removed by conventional means for example by reaction with trifluoroacetic acid in a solvent such as dichloromethane. The compound of formula (III) wherein A is the chain —$(CH_2)_p$NH— thus obtained may then be converted into a compound of formula (II) wherein A is the chain $(CH_2)_p NR_3$ wherein $R_3$ is alkyl by a conventional alkylation reaction. For example by alkylation using the appropriate alkyl trifluoromethylsulphonate in a solvent such as dichloromethane.

Compounds of formula (III) wherein A is the group $(CH_2)_pO$ where p is 1 or 2 may be prepared by reaction of the hydroxylamine $R_1NHOH$ with the halo acyl halide (XI) in the presence of a base such as potassium carbonate and in a polar solvent such as N,N-dimethylformamide.

The hydroxylamine $R_1NHOH$ may be prepared from the corresponding nitro compound $R_1NO_2$ in a conventional manner e.g. reaction with hydrazine in the presence of a 5% rhodium on carbon catalyst.

In order that the invention may be more fully understood the following examples are given by way of illustration only.

In the intermediates and Examples unless otherwise stated:

Melting points (m.p.) were determined on a Gallenkamp m.p. apparatus or a Buchi capillary apparatus and are uncorrected. All temperature refers to °C. Infrared spectra were measured on a FT-IR instrument. Proton Magnetic Resonance ($^1$H-NMR) spectra were recorded at300 Mhz or 400 MHz, chemical shifts are reported in ppm downfield (d) from $Me_4Si$, used as internal standard, and are assigned as singlets (s), doublets (d), doublets of doublets (dd), triplets (t), quartets (q) or multiplets (m). Colum chromathography was carried out over silica gel (Merck AG Damstaadt, Germany). The following abbreviations are used in text: EA=ethyl acetate, CH=cyclohexane, DCM=dichloromethane. DMSO=dimethylsulphoxide, DBU=1,8-diazabicyclo [5.4.0] undec-7-ene.

Tlc refers to thin layer chromatography on silica plates. Solution were dried over anhydrous sodium sulphate. Tetrahydrofuran (THF) was freshly distilled from K/benzophenone under nitrogen atmosphere; reagent grade cyclohexane and ethyl acetate were used without further purification. All chromatography was done using silica gel, 230–400 mesh, (Merck). Yields are reported for isolated products which were pure by NMR and Tlc.

Intermediate 1

Ethyl 4,6-dichloroindole-2-carboxylate

To a solution of ethyl pyruvate (2.05 ml), in absolute ethanol (38 ml), concentrated sulphuric acid (0.5 ml) was added slowly under vigorous stirring. The resulting mixture was stirred at 30° for 10 minutes, then 3,5-dichlorophenylhydrazine hydrochloride (4 g) was added portionwise. The mixture was heated to reflux for 4 hours, cooled to 23°, poured into cold water (500 ml) and extracted with diethyl ether (3×300 ml). The organic layers were separated and dried. The solvent was evaporated under reduced pressure to give the 2-(3,5-dichlorophenylhydrazone)propionic acid ethyl ester as yellow solid (5 g; tlc DCM, Rf=0.79, 0.47) in E and Z isomers mixture. The solid was added to polyphosphoric acid (20 g) under stirring and the mixture was heated at 45° for 20 minutes to give a brown product which was crystallized by 95% ethanol (300 ml) to obtain the title compound as a yellow-brown solid (3.3 g; m.p. 180°; Tlc DCM Rf=0.54). IR(CDCl$_3$) Vmax(cm$^{-1}$)3440(NH), 1772–1709(C=O). $^1$H-NMR(CDCl$_3$)9.00(s), 7.28(d), 4.42(q), 1.42(t).

Intermediate 2
Ethyl 3-formyl-4,6-dichloroindole-2-carboxylate

A solution of N-methyl formanilide (5.19 g) and phosporous axychloride (5.53 g) was stirred at 23° for 15 minutes. 1,2-Dichloroethane (60 ml) and intermediate 1 (6 g) were added and the resulting suspension was stirred at 80° for 6 hours. The reaction mixture was poured into a 50% aqueous solution of sodium acetate (300 ml) to give, by filtration, the title compound as a yellow solid (4.1 g; tlc EA/CH:4/6, Rf=0.4). IR(Nujol) Vmax(cm$^{-1}$) 1726 (C=O), 1663 (C=O), 1556 (C=C), 2725–2669 (CH). $^1$H-NMR (DMSO) 13.15(s), 10.60(s), 7.54(d), 7.40(d), 4.43(q), 1.36 (t).

Intermediate 3
Ethyl 3-formyl-1-(2-trimethylsilyl-ethoxymethyl)-4,6-dichloroindole-2-carboxylate To a cooled solution of intermediate (2) (700 mg) in dry DMF (20 ml) at 0° was added lithium bis-trimethylsilylamide (3.7 ml, 1M solution) in THF. The mixture was stirred for 15 minutes at 0°, then tri-methylsilylethoxymethyl chloride (0.817 g) was added. After one hour the resulting mixture was poured into water (25 ml) and extracted with ethyl acetate (3×20 ml). The combined organic layers were dried and concentrated under vacuum. The residue was purified by chromatography on silica gel to afford the title compound (950 mg) as a pale yellow solid. Rf=0.3 EA/CH: 1.9.

Intermediate 4
Methyl (Z)-4,6-dichloro-3-(2-oxo-1-phenyl-pyrrolidin-3-ylidenemethyl)-1-(2-trimethylsilyl-ethoxymethyl)-1H-indole-2-carboxylate 1-phenyl-2-pyrrolidinone (426 mg) was dissolved in THF (10 ml), the solution cooled to −78° and tert-butyllithium (1.80 ml, 1.6M solution in hexanes) slowly added; to the resulting solution, stirred at this temperature for 1.5 h, intermediate 3 (1 g) dissolved in THF (10 ml) was added and stirring continued at −78° for 3 h. The reaction was then allowed to warm to room temperature over 3 h and stirred for another 1.5 h. The reaction was quenched with 20 ml of saturated NH$_4$Cl solution, ethyl acetate (50 ml) was added and the organic phase separated and washed with 0.1 M hydrochloric acid (2×20 ml), water (20 ml), brine (10 ml), and dried. The solvent was evaporated, the residue dissolved in 20 ml of dichloromethane/methanol (4/1) and treated at room temperature with trimethylsilyldiazomethane (1.70 ml, 2M solution in hexanes) for 30 min. Final purification by column chromatography (CH/EA 8/2) yielded the title compound (740 mg), as a white solid. IR (nujol) Vmax (cm−1) 1709 (C=O), 1684 (C=O). $^1$H NMR (CDCl3) 7.85 (t), 7.80 (d), 7.50 (d) 7.40 (t), 7.20 (d), 7.17 (t), 5.89 (s), 3.90 (s), 3.86 (t), 3.53 (t), 2.64 (td), 0.88 (t), −0.05 (s).

Intermediate 5
Methyl (Z)-4,6-dichloro-3-(2-oxo-1-phenyl-piperidin-3-ylidenemethyl)-1-(2-trimethylsilyl-ethoxymethyl)-1H-indole-2-carboxylate N-phenylpiperidinone (370 mg) was dissolved in THF (10 ml), the solution cooled to −78°, tert-butyllithium (1.30 ml, 1.6M solution in hexanes) was added and to the resulting mixture stirred at this temperature for 1.5 h. intermediate 3 (800 mg) dissolved in THF (10 ml) was added and then stirring continued at −78° for 3 h. The reaction was then allowed to warm to room temperature over 3 h and stirred for another 1.5 h. The reaction was quenched with 20 ml of saturated NH$_4$Cl solution, ethyl acetate (50 ml) was added and the organic phase separated and washed with 0.1 M hydrochloric acid (2×20 ml), water (20 ml), brine (10 ml), and dried. The solvent was evaporated and the residue redissolved in 20 ml of dichloromethane/methanol (4/1) and treated at room temperature with trimethylsilyldiazomethane (1.50 ml, 2M solution in hexanes) for 30 min. Final purification by column chromatography (CH/EA 7/3) yielded the title compound (700 mg) as a white solid. IR (nujol) Vmax (cm−1) 1713 (C=O), 1672 (C=O). $^1$H NMR (CDCl3) 8.09 (t), 7.48 (d), 7.40 (m), 7.26 (tt), 7.18 (d), 5.90 (s), 3.89 (s), 3.76 (t), 3.52 (m), 2.41 (td), 1.95 (m), 0.87 (t), 0.06 (s).

Intermediate 6
1-tert-butoxycarbonyl-2-phenyl hydrazine di tert-butyl dicarbonate (5.6 g) was added to a solution of phenyl hydrazine (2.5 ml) in tetrahydrofuran (50 ml). The solution was stirred at 25° for 2 hrs then concentrated in vacuo affording the crude title compound (5.44 g). T.l.c. EA/CH (1/2), Rf=0.8. I.R.(cm−1):1724(C=O), 1605 (C=C).

Intermediate 7
1-tert-butoxycarbonyl-2-phenyl-pyrazolidin-3-one

To a solution of intermediate 6 (5.4 g) in dry dimethylformamide (50 ml) was added potassium carbonate (6.9 g) and after 5 min. chloro propionyl chloride (2.4 ml). The resulting mixture was stirred at 25° for 2 hrs, then diluted with diethyl ether (200 ml), washed with water (2×200 ml), dried and concentrated in vacuo. The crude compound obtained was crystallized from ethyl acetate/n-hexane to give the title compound (5.9 g). T.l.c. diethyl ether/petroleum ether (1/1), Rf=0.4. mp.=150°.

Intermediate 8
Ethyl 4,6-dichloro-3-formyl-1-tert-butoxycarbonyl-1H-indole-2-carboxylate To a suspension of 4,6-dichloro-3-formyl-1H-indole-2-carboxylic acid ethyl ester (8 g) in dry tetrahydrofuran (100 ml) were added di-tert-butyl dicarbonate (7.3 g) and 4-dimethylaminopyridine (0.7 g). The reaction mixture was stirred at 25° for 2 hrs, then diluted with ethyl acetate (300 ml), washed with ammonium chloride (sat.) (200 ml), brine (200 ml), dried and concentrated in vacuo. The crude title compound was crystallized from ethyl acetate (8.6 g). T.l.c. EA./CH (1/2), Rf=0.8. mp.=141°.

Intermediate 9
1-tert-butoxycarbonyl-2-(4-nitrophenyl) hydrazine

Di tert-butyl dicarbonate (7.8 g) was added to a solution of phenyl hydrazine (2.5 ml) in tetrahydrofuran (100 ml). The solution was stirred at 25° for 2 hrs then concentrated in vacuo affording the crude product which was crystallized from ethyl acetate/n-hexane (1/3) to give the title compound (6.9 g), T.l.c. EA/CH (1/2), Rf=0.85. mp=120°.

Intermediate 10
1-tert-butoxycarbonyl-2-(4-aminophenyl) hydrazine

A solution of sodium hydrosulfite (20 g) and potassium carbonate (22 g) in water (200 ml) was added to a solution of intermediate 9 (6 g) in ethanol (350 ml). The resulting mixture was stirred at 25° for 1 hr, then concentrated in vacuo and extracted with ethyl acetate (200 ml). The organic phase was washed with ammonium chloride (sat.) (2×200 ml), dried and concentrated in vacuo. The crude compound was purified by silica gel column chromatography using EA/CH (1/2) as eluant to give the title compound (3 g). T.l.c. EA/CH (1/1), $R_f$=0.2. mp.=128°.

Intermediate 11

1-tert-butoxycarbonyl-2-[4(-tert-butoxycarbonylamino) phenyl]hydrazine

Di tert-butyl dicarbonate (3.33 g) was added to a solution of intermediate 10 (3.41 g) in tetrahydrofuran (100 ml). The solution was stirred at 25° for 15 hrs then concentrated in vacuo affording the crude title compound which was crystallized from ethyl acetate/n-hexane (4.4 g). T.l.c. EA/CH (1/2), Rf=0.90. mp.=155°.

Intermediate 12

1-tert-butoxycarbonyl-2-[(4-tert-butoxycarbonylamino) phenyl]pyrazolidin-3-one

To a solution of intermediate 11 (0.5 g) in dry dimethylformamide (5 ml) was added potassium carbonate (0.213 g) and after 15 min. chloro propionyl chloride (0.15 ml). The resulting mixture was stirred at 25° for 20 hrs then diluted with diethyl ether (50 ml). It was the washed with water (50 ml) and ammonium chloride (sat.) (50 ml). After drying, the solution was concentrated in vacuo to give the crude compound which was crystallized from ethyl acetate/n-hexane (1/4) to give the title compound (0.252 g). T.l.c. EA/CH (1/1), Rf=0.60. mp.=178°.

Intermediate 13

4,6-Dichloroindole-3-formyl-2-carboxylic acid

To a suspension of the intermediate (2) (7.0 g), in ethyl alcohol (250 ml) lithium hydroxide (2.26 g) was added. The yellow solution was heated at 50° for 8 hours then acidified with HCl till pH=2. The precipitate was collected by filtration to furnish the title compound as a white solid (6.29) mp=235–240°.

Intermediate 13a 4,6-Dichloroindole-3-formyl-2-carboxylic acid tert-butyl ester

To a refluxing suspension of intermediate 13 (1.0 g.) in dry toluene (50 ml) N,N-dimethylformamide di-tert-butyl acetal (4.38 g.) was slowly added. The heating continued for 30 minutes then the dark solution was cooled and washed with water, sodium bicarbonate solution and, brine. The organic layer was dried and the solvent removed under reduced pressure. The residue was purified by flash chromatography (CH/EA=8/2$R_f$=0.33) to give the title compound as a white solid (470 mg). IR (Nujol) $v_{max}$(cm$^{-1}$) 3335 (N—H), 1724 (C=O) and 1663 (C=O).

Intermediate 14

4,6-Dichloroindole-3-formyl-1-tetbutyloxycarbonyl-2-carboxylic acid -tert-butyl ester To a solution of intermediate 13a (470 mg.) in dry THF (10 ml), 4-dimethylaminopyridine (22 mg) and a solution of di-tert-butyl dicarbonate (392 mg) in dry THF (5 ml) were added. The solution was stirred for 30 minutes then the solvent removed under reduced pressure. The residue was purified by flash chromatography (CH/EA=9/1 $R_f$=0.38) to give the title compound as a foam. (468 mg). IR (Nujol) $v_{max}$(cm$^{-1}$) 1765 (C=O), 1740 (C=O) and 1688 (C=O).

Intermediate 15

N-(Phenylaminocarbonyl)-α-phosphonoglycine trimethyl ester

A solution of N-(Benzyloxycarbonyl)-α-phosphonoglycine trimethyl ester (3 g.) in methanol (50 ml) was hydrogenated under a 1 atm. pressure for 5 hrs in the presence of 5% palladium on carbon (0.55 g.). The catalyst was filtered off on celite and the solution was evaporated under reduced pressure. The residue was dissolved in dichloromethane (15 ml), phenyl isocyanate (1.1 ml) was added and the reaction mixture was stirred for 15 hrs. The solvent was evaporated under reduced pressure and the residue was triturated in diethyl ether (50 ml) to give the title compound as a white powder (2.4 g m.p. 144–146° IR (Nujol) $v_{max}$ (cm$^{-1}$) 1745 (C=O), 1707 (C=O)

Intermediate 16

(Z) 4,6-Dichloroindole-3-(2,5-dioxo-1-phenyl-imidazolidin-4-ylidenemethyl)-indole-1,2-dicarboxylic acid 1,2 di-tertbutyl ester)

To a solution of intermediate 15 (367 mg) in dry THF (8 ml), DBU (352 mg.) was added dropwise. The solution was stirred at room temperature for 10 minutes, then a solution of intermediate 16 (480 mg) in dry THF (10 ml) was slowly added. The mixture was stirred for 15 minutes, diluted with ethyl acetate (10 ml) and quenched with ammonium chloride. The organic layer was dried and the solvent evaporated under reduced pressure. The residue was purified by flash chromatography (CH/EA=85/15 $R_f$=0.33) to give the title compound as a foam (284 mg). IR (Nujol) $v_{max}$(cm$^{-1}$) 1772 (C=O), 1726 (C=O) and 1678 (C=O).

Intermediate 17

4,6-Dichloroindole-3-formyl-2-carboxylic acid allyl ester

To a suspension of intermediate of intermediate 2 (3.0 g) in allyl alcohol (100 ml) p-toluenesulfonic acid monohydrate (2.0 g) was added. The suspension was heated at 90° for 2.5 hours, then the solvent removed under reduced pressure. The residue was dissolved in methylene chloride, washed with a solution of Na$_2$CO$_3$ (10%), water and purified by flash chromatography (CH/EA=7/3 $R_f$=0.34) to give the title compound as a white solid (1.10 g). IR (Nujol) $v_{max}$ (cm$^{-1}$) 1720 (C=O) and 1657 (C=O). $^1$H-NMR (DMSO) 13.20 (bs), 10.61 (s), 7.55 (d), 7.42 (d), 6.14–6.0 (m), 5.46 (dd), 5.33 (dd) and 4.92 (d). m/z (FAB) 298 (MH).

Intermediate 18

4,6-Dichloroindole-1-tet-butyloxycarbonyl-3-formyl-2-carboxylic acid allyl ester To a solution of intermediate 17 (1.10 g) in dry THF (40 ml), 4-dimethylaminopyridine (49 mg) and a solution of di-tert-butyl dicarbonate (886 mg) in dry THF (10 ml), were added. The solution was stirred for 1 hours then the solvent removed under reduced pressure. The residue was purified by flash chromatography (CH/EA=9/1 $R_f$=0.37) to give the title compound as a white solid (853 mg; mp.=106.9–107.7). IR (Nujol) $v_{max}$(cm$^{-1}$) 1757–1744 (C=O) and 1682 (C=O).

Intermediate 19

(E) 4,6-Dichloro-3-(2,5-dioxo-1-phenyl-imidazolidin-4-ylidenemethyl)-indole-1,2-dicarboxylic acid 2-allyl ester 1-tertbutyl ester To a solution of intermediate 15 (590 mg) in dry THF (10 ml) DBU (566 mg) was added dropwise. The solution was stirred at room temperature for 10 minutes, then a solution of intermediate 18 (740 mg) in dry THF (15 ml) was slowly added. The mixture was stirred for 15 minutes, diluted with ethyl acetate (10 ml) and quenched with ammonium chloride. The organic layer was dried and the solvent evaporated under reduced pressure. The residue was purified by flash chromatography (CH/EA=7/3 $R_f$=0.27) to give the title compound as a foam (369 mg). IR (Nujol) $v_{max}$(cm$^{-1}$) 3331 (N—H), 1730 (C=O), 1673 (C=O) and 1533 (C=C).

Intermediate 20

E-3-[(1-tert-butoxycarbonyl-3-oxo-2-phenyl)pyrazolidin-4-ylidene methyl]-4,6-dichloro-1-tert-butoxycarbonyl-1H-indole-2-carboxylic acid tert butyl ester To a solution of Example 15 (0.7 g) in dry tetrahydrofuran (50 ml) were added di-tert-butyl-di-carbonate (0.33 g) and 4-dimethylaminopyridine (0.03 g). The solution was stirred at 25° for 30 min. then diluted with diethyl ether (200 ml), washed with ammonium chloride (sat.) (200 ml), brine (200 ml), dried and concentrated in vacuo. The crude title compound was purified by silica gel column chromatography using diethyl ether and petrol (2/8) as eluant to give the title compound (0.54 g). T.l.c. diethyl ether/petrol (5/25), $R_f$=0.45. 1H-NMR(CDCl$_3$): 1.27(s, 9H), 1.52(s, 9H), 1.67(s, 9H), 4.65(d, 2H), 7.18(t, 1H), 7.27(d, 1H), 7.39(m, 2H), 7.65(m, 1H), 7.66(m, 2H), 8.04(d, 1H).

Intermediate 21
(Z) 3-[(1-tert-butoxycarbonyl-3-oxo-2-phenyl)pyrazolidin-4-ylidene methyl]-4,6-dichloro-1-tert-butoxycarbonyl-1H-indole-2-carboxylic acid tert butyl ester A solution of intermediate 20 (0.53 g) in acetonitrile (30 ml) was irradiated using a 400 Watt mercury lamp for 45 min. The solution was concentrated in vacuo to give a mixture of the two isomers that were separated by silica gel column chromatography using ethyl acetate/cyclohexane (5/95) as eluant to obtain the title compound 6 (0.13 g), T.l.c. EA/CH (5/25), $R_f$=0.85. 1H-NMR(CDCl$_3$): 1.27(s, 9H), 1.51(s, 9H), 1.65(s, 9H), 4.86(m, 2H), 7.07(m, 1H), 7.09(m, 1H), 7.20(d, 1H), 7.28(m, 2H), 7.57(m, 2H), 7.97(d, 1H).

Intermediate 22
1-tert-butoxycarbonyl-2-(4-methylsulfamidophenyl) hydrazine

To a solution of intermediate 10 (0.2 g) in tetrahydrofuran (5 ml) under nitrogen at 0° C. was added pyridine (0.045 ml). After 5 minutes methanesulfonyl chloride (0.045 ml) was added dropwise to the stirred solution. The reaction mixture was allowed to warm up to room temperature. After 1 hour saturated ammonium chloride solution (20 ml) was added and the reaction mixture extracted with ethyl acetate (3×10 ml) and the combined extracts dried. The solvent was removed by distillation under reduced pressure and the product purified by flash column chromatography over silica gel CH/EA yielding the title compound as a yellow solid (0.140 g). I.R. (cm −1, Nujol): 3302 (NH), 1709 (C=O), 1600 (C=C), 1323–1151 (SO2).

Intermediate 23
-1-tert-butoxycarbonyl-2-(4-methylsulfamidophenyl)-pyrazolidin-3-one To a stirred solution of Intermediate 22 (0.6 g) in dry dimethylformamide (15 ml) under nitrogen at 0° was added pyridine (0.23 ml). Chloro propionyl chloride (0.2 ml) was then added dropwise to the solution. The mixture reaction was stirred at 25° C. for 2 hrs diluted with ethyl acetate (50 ml), and then washed with water (50 ml) and saturated ammonium chloride solution (50 ml). The organic solution was dried and then concentrated in vacuo to give crude 1-tert-butoxycarbonyl-2-(4-methylsulfamidophenyl)-2-(3-chloropropionyl)hydrazine as a yellow oil. This was dissolved in dimethylformamide (5 ml) under nitrogen and at 25° anhydrous potassium carbonate (0.450 g) was added. The resulting mixture was stirred for 1 hr then diluted with saturated ammonium chloride solution (50 ml). The aqueous solution was extracted with ethyl acetate (3×50) and the combined organic phases were dried and concentrated in vacuo. The crude residue was purified by silica gel flash column chromatography eluting with diethyl ether to give the title compound (0.25 g). 1H-NMR(DMSO);1.28(s,9H), 2.73(t,2H), 2.93(s,3H), 4.06(t,2H), 7.19(d,2H), 7.42(d,2H), 9.66(s,1H). I.R. (cm−1,Nujol):3252–3202(NH), 1693 (C=O), 1600(C=C), 1310–1151(SO2).

Intermediate 24
2-phenyl-pyrazolidin-3-one

Intermediate 7 (4.6 g) was dissolved in dry dichloromethane (10 ml) and trifluoroacetic acid (10 ml). The resulting solution was stirred at 25° for 1 hr then concentrated in vacuo. The residue was dissolved in ethyl acetate (100 ml), washed with sodium bicarbonate (sat.) (2×100 ml), brine (100 ml), dried and concentrated in vacuo to give the crude title compound (2.6 g). T.l.c. CH/EA (1/1), $R_f$=0.30 1H-NMR (CDCl$_3$); 2.78(t,2H), 3.52(q,2H), 4.75(t, 1H), 7.12 (tt, 1H), 7.36(t, 2H), 7.85(d, 2H). I.R. (cm−1): 3238(NH), 1674(C=O).

Intermediate 25
1-methyl-2-phenyl-pyrazolidin-3-one

To a solution of intermediate 24 (1.43 g) in dimethylformammide (20 ml) was added dropwise and at −20° methyl trifluoromethanesulfonate ((1.4 ml). The reaction mixture was allowed to warm-up to 25° and after 3 hrs was diluted with diethyl ether (200 ml), washed with ammonium chloride (sat.) (200 ml), water (200 ml), dried and concentrated in vacuo. The crude compound was purified by silica gel column chromatography using ethyl acetate/cyclohexane (3/7) as eluant to give the title compound (0.4 g). T.l.c. CH/EA (1/1), $R_f$=0.42. I.R. (cm−1): 1697 (C=O).

Intermediate 26
N-(3-chloropropionyl)-N-phenylhydroxylamine

To a suspension of rhodium on carbon 5% (0.13 g) in dry tetrahydrofuran (23 ml) was added nitrobenzene (5 g). The mixture was cooled at 0° and hydrazine hydrate (2 g) was added dropwise. The temperature of the mixture is maintained at 25–30° throughout the addition; after the reaction was stirred at 25° for 2 hrs then filtered and the catalyst washed with a little tetrahydrofuran. The solution was concentrated in vacuum and the residue was dissolved in dimethylformamide (30 ml) and cooled at −5°, then potassium carbonate (5.6 g) and, after 10 min., chloro propionyl chloride (3.8 ml) were added. The reaction mixture was stirred at 25° for 1 hr then diluted with diethyl ether (150 ml), washed with water (2×200 ml), dried and concentrated in vacuo. The residue was purified by crystallization using ethyl acetate/cyclohexane to give the title compound as a solid (4 g). T.l.c CH/EA 1/2 $R_f$=0.3. 1H-NMR (CDCl$_3$): 2.7(bs, 2H), 3.8(t, 2H), 7.5(bm, 5H). I.R. (cm−1): 1645 (C=O), 1626(C=C).

Intermediate 27
3-oxo-2-phenyl-isoxazolidine

To a solution of intermediate 26 (3.35 g) in acetone (150 ml) was added potassium carbonate (2.3 g). The reaction mixture was stirred at 25° for 6 hrs then concentrated in vacuo. The residue was triturated with ethyl acetate, filtered and concentrated in vacuo to obtain the crude title compound as an oil (2.5 g). T.l.c. CH/EA 1/2, $R_f$=0.3. 1H-NMR CDCl$_3$): 3.0(t, 2H), 4.52(t, 2H), 7.14(tt, 1H), 7.37(m, 2H), 7.69(m, 2H). I.R. (cm−1): 1697(C=O).

Intermediate 28
1-tert-butoxycarbonyl-2-(3-nitrophenyl) hydrazine

To a solution of 3-nitrophenyl hydrazine (6 g) in dioxane (60 ml) and water (30 ml) were added sodium hydroxide 1M (30 ml) and di tert-butyl dicarbonate (7.6 g). The solution was stirred at 25° for 2 hrs then concentrated in vacuo; diluted in ethyl acetate (200 ml), washed with ammonium chloride (sat.) (2×200 ml), brine (2×200 ml), dried and concentrated in vacuo to give the crude intermediate which was purified by trituration with ethyl acetate/cyclohexane (19/29) to obtain the title compound (4.3 g,), T.I.c. EA/CH (1/1), RF=0.85, m.p.=105°.

Intermediate 28a
1-tert-butyloxycarbonyl-2-(3-tert-butoxycarbonylamino) phenylhydrazine To a solution of intermediate 28 (3.64 g) in ethanol (70 ml) were added iron powder (7.0 g) and calcium chloride (0.71 g). The reaction mixture was heated at 70° C. for 20 hrs then filtered over silica gel washing with ethyl acetate. The solution was dried and concentrated in vacuo to afford the 1-tert-butyloxycarbonyl-2-(3-aminophenyl) hydrazine (3.0 g) that was dissolved in dry tetrahydrofuran (100 ml) and di-tert-butyl-di-carbonate (3.68 g) was added. The reaction mixture was stirred at 25° for 20 hrs than concentrated in vacuo. The product was purified by trituration with ethyl acetate to give the title compound (3.73 g). T.I.c. EA/CH (1/1); $R_f$=0.7.

I.R. (cm−1); 3329 and 3294(NH), 1715 and 1697 (C═O), 1610(C═C),

Intermediate 29

1-tert-butyloxycarbonyl-2-[3-tert-butoxycarbonylamino) phenyl]pyrazolidin-3-one

To a solution of intermediate 28a (0.316 g) in dry dimethylformamide (4.0 ml) was added potassium carbonate (0.142 g) and after 15 min. chloro propionyl chloride (0.098 ml). The resulting mixture was stirred at 25° for 3 hrs then diluted with diethyl ether (50 ml), washed with ammonium chloride (sat.) (50 ml) and brine (50 ml). After drying, the solution was concentrated in vacuo and the residue (0.4 g) was dissolved in dimethylformamide (4.78 ml). Potassium carbonate (0.139 g) was added and the mixture stirred at 25° for 3 hours. The reaction mixture was then diluted with diethyl ether (50 ml) washed with ammonium chloride (sat.) (50 ml) and brine (50 ml). After drying, the solution was concentrated in vacuo to give the crude compound (0.4 g) which was purified by silica gel column chromatography using ethyl acetate/cyclohexane (1/3) as eluant to obtain the title compound (0.27 g). T.I.c. EA/CH (⅓) $R_f$=0.25. m.p.=129°.

Intermediate 30 and intermediate 31

(E)3-[(1-tert-butyloxycarbonyl-2[(3-tert-butoxycarbonylamino)phenyl]-3-oxo) pyrazolidin-4-ylidene methyl]-4,6-dichloro-1H-indole-2-carboxylic acid tert butyl ester (30)

(E)3-[(1-tert-butyloxycarbonyl-2[(3-tert-butoxycarbonylamino)phenyl]-3-oxo) pyrazolidin-4-ylidene methyl]-4,6-dichloro-1tert-butyloxycarbonyl-1H-indole-2-carboxylic acid tert butyl ester (31)

To a solution of intermediate 4 (0.196 g) in dry tetrahydrofuran (5 ml) was added dropwise, at 31 78° a solution of lithium bis(trimethylsilyl)amide 1M in tetrahydrofuran (0.564 ml). The reaction mixture was allowed to warm up to −20° in 30 min, then a solution of 4,6-dichloro-3-formyl-1-[N-tert-butyloxycarbonyl]-1H-indole-2-carboxylic acid tert butyl ester (0.18 g) in dry tetrahydrofuran (4 ml) was added. The solution was diluted with ethyl acetate (50 ml) and washed ammonium chloride (50 ml), brine (50 ml), dried and concentrated in vacuo The crude compound was purified by silica gel column chromatography using ethyl acetate/cyclohexane (3/97) as eluant to give the Intermediate 38 [(0.05 g), T.I.c. EA/CH (½), $R_f$=0.5]and Intermediate 39 [(0.04 g), T.I.c. EA/CH Intermediate 30

1H—NMR (DMSO); 1.21(s,9H), 1.45(s,9H), 151(s,9H), 4.49(d, 2H), 7.18(m, 1H), 7.3–7.2(m,2H). 7.30(d,1H), 7.50 (d,1H), 7.74(t,1H), 7.82 (t,1H), 9.43(s, 1H), 12.4(bs,1H). I.R. (cm−1): 3346(NH), 1728 and 1684(C═O), ms (m/z): 773, 758, 673, 561.

Intermediate 31

1H—NMR (DMSO); 1.23(s,9H), 1.45(s,18H), 1.61(s,9H), 4.57(d,2H), 7.18(m, 1H), 7.25(m,2 H), 7.49(t,1H), 7.57(d, 1H), 7.82(bs,1H), 7.94(d,1H), 9.44(s, 1H). I.R. (cm−1); 3341(NH), 1726(C═O). ms (m/z): 773,242.

Intermediate 32

(E) 4,6-dichloro-3-(2,5-dioxo-1-phenyl-pyrrolidin-3-ylidenemethyl)-indole-1,2-dicarboxylic acid di-tert-butyl-ester To a solution of intermediate 14 (440 mg) in dry toluene (20 ml) the N-phenyltriphenylphosphoranylidene succinimide (472 mg) was added. The solution was heated at 70° for 21 hours then more succinimide (236 mg) was added and the heating continued for 10 hours. The solvent was removed under reduced pressure and the residue purified by flash chromatography (CH/EA=8/2 $R_f$=0.38) to give the title compound as a white solid (309 mg).

IR (Nujol)$\nu_{max}$(cm−1)1750 (C═O).

Intermediate 33

1-tert-butyloxycarbonyl-3-oxo-2-phenyl-tetrahydro-pyridazine

To a solution of Intermediate 6 (1 g) in dry dimethylformamide (10 ml) was added pyridine (0.78 ml), and 4-bromobutyryl chloride (0.83 ml), under nitrogen at 25°, and the reaction mixture was stirred for 15 hrs. The solution was diluted with diethyl ether (80 ml), and washed with brine (2×80 ml). After drying, the organic solution was concentrated in vacuo to give a yellow oil (1.7 g). To a solution of this oil (2.25 g) in dimethylformamide (15 ml), under nitrogen at 25°, anhydrous potassium carbonate (1.7 g) was added and the resulting mixture was stirred for 3 hr. The solution was diluted with diethyl ether (100 ml), washed with brine (2×80 ml), dried and concentrated in vacuo. The crude residue was purified by silica gel flash column chromatography using cyclohexane/ethyl acetate (8/2) as eluant to give title compound (1.4 g) as a white powder. T.I.c. EA/CH (1/1) $R_f$=0.60.

Intermediate 34

2-quinolinylhydrazine

To a solution of 2-chloroquinoline (15 g) in ethanol (150 ml) was added hydrazine hydrate (40 ml), the resulting solution was heated at reflux for 6 hours then diluted with water (400 ml) and extracted with diethyl ether (3×200 ml). The collected organic phase was washed with brine (300 ml), dried and concentrated under vacuum to afforg the title compound as a solid (13 g), 1H—NRM (DMSO); 4.29(s,2H), 6.83 (d,1H), 7.15(m,1H), 7.47(m,1H), 7.52(d, 1H), 7.62(dd, 1H), 7.86(d,1H), 8.05(s,1H)

Intermediate 35

1-tert-butyloxycarbonyl-2-(2-quinolinyl)hydrazine

To a solution of intermediate 34 (13 g) in tetrahydrofuran (150 ml) was added di-tert-butyl dicarbonate (18 g). The solution was stirred at 25° for 1 hr then concentrated in vacuo and triturated with ethyl acetate/n-hexane to obtain the title compound (19 g). T.I.c. EA/CH (1/2), $R_f$=0.3,m.p.= 148°–150°.

Intermediate 36

1tert-butyloxycarbonyl-2-[3-chloropropanoyl-2-quinolinyl]-hydrazine

To a solution of intermediate 35 (5 g) in tetrahydrofuran (60 ml) was added dropwise and a 0° a solution of chloro propionyl chloride (0.92 ml) in tetrahydrofuran (40 ml). The resulting heterogeneous solution was stirred at 0° for 30 min., filtered and concentrated in vacuo to give the title compound (2.7 g) as a foam, T.I.c. EA/CH (1/1), $R_f$=0.8.

Intermediate 37

1-tert-butyloxycarbonyl-2-(2-quinolinyl)-pyrazolidin-3-one

Potassium carbonate (1.3 g) was added to a solution of Intermediate 36 (2.7 g) dissolved in dimethylformamide (30 ml). The reaction mixture was stirred at 25° for 2 hrs then diluted with diethyl ether (100 ml), washed with water (100 ml), dried and concentrated in vacuo. The crude product was purified by silica gel column chromatography using ethyl acetate/cyclohexane (2/8) as eluant to obtain the title compound (0.84 g) as a foam. T.l.c. EA/CH (1/1); $R_f$=0.6. m.p.=112°.

Intermediate 38

(E)3-[1-tert-butoxycarbonyl-2-(2-quinolinyl)-3-oxo]pyrazolidin-4-ylidene methyl]-4,6-dichloro-1-tert-butoxycarbonyl-1H-indole-2carboxylic acid tert butyl ester A solution of intermediate 37 (0.17 g) in dry tetrahydrofuran (10 ml) was added dropwise, at –78° a solution of lithium bis(trimethylsilyl)amide 1M in tetrahydrofuran (0.62 ml). The reaction mixture was allowed to warm up to –20° in 30 min, then a solution of 4,6-dichloro-3-formyl-1-[N-tert-butoxycarbonyl]-1H-indole-2-carboxylic acid tert butyl ester (0.2 g) in dry tetrahydrofuran (10 ml) was added. The solution was maintained at –20° for 30 min. then warmed up to 25° C. for 2 hrs. The solution was diluted with hydrochloric acid (50 ml), extracted with diethyl ether (3×40 ml) and the collected organic phase dried and concentrated in vacuo. The crude compound was purified by silica gel column chromatography using EA/CH (1/9) as eluant to give the title compound (0.125 g), T.l.c. EA/CH (1/2), $R_f$=0.7 m.p.=48°51°.

Intermediate 39

1-tert-butoxycarbonyl-2-(2-pyridyl)hydrazine 2-chloropyridine (23 g) was added to hydrazine hydrate (110 ml). The resulting solution was heated at reflux for 6 hrs then extracted with diethyl ether (2×100 ml).

The aqueous phase was concentrated in vacuo, diluted with water (40 ml) then potassium hydroxide (2 g) was added and the solution extracted with diethyl ether (100 ml). The collected organic phase was dried and concentrated in vacuo to afforg the crude 2-pyridine-hydrazine intermediate as a solid (13 g) that was dissolved in tetrahydrofuran (200 ml) and di-tert-butyl dicarbonate (26 g) was added. The solution was stirred at 25° for 1 hr then concentrated in vacuo and triturated from ethyl acetate/n-hexane to obtain the title compound (16 g), T.l.c. EA/CH (2/1), $R_f$=0.54, m.p.=91° C.

Intermediate 40

1-tert-butoxycarbonyl-2(3-chloropropanoyl-2-pyridyl)-hydrazine

To a solution of intermediate 39 (4 g) in tetrahydrofuran (60 ml) was added dropwise and at 0° a solution of chloro propionyl chloride (0.92 ml) in tetrahydrofuran (40 ml). The resulting heterogeneous mixture was stirred at 0° for 30 min, filtered and concentrated in vacuo to give the crude title compound as a foam, T.l.c. EA/CH (1/1), $R_f$=0.8.

Intermediate 41

1-tert-butoxycarbonyl-2-(2-pyridyl)-pyrazolidin-3-one

Potassium carbonate (1.3 g) was added to a solution of Intermediate 40 dissolved in dimethylformamide (30 ml). The reaction mixture was stirred at 25° for 2 hr diluted with diethyl ether (100 ml), washed with water (100 ml), dried and concentrated in vacuo. The crude product was purified by silica gel column chromatography using ethyl acetate/cyclohexane (2/8) as eluant to obtain the title compound (0.87 g) as a foam, T.l.c. EA/CH (1/1); $R_f$=0.65. 1H—NMR (CDCl$_3$): 1.50(s, 9H), 2.59(t, 2H), 4.27(m, 2H), 6.81(dd, 1H), 6.96(m, 1H), 7.63(m, 1H), 8.33(m, 1H).

Intermediate 42

(E)3-[1-tert-butoxycarbonyl-2-(2-pyridyl)-3-oxo]pyrazolidin-4-ylidene methyl]-4,6-dichloro-1tert-butoxycarbonyl-1H-indole-2-carboxylic acid tert butyl ester To a solution of intermediate 41 (0.361 g) in dry tetrahydrofuran (10 ml) was added dropwise, at 31 78° a solution of lithium bis(trimethylsilyl)amide 1M in tetrahydrofuran (1.6 ml). The reaction mixture was allowed to warm up to –20° in 30 min, then a solution of 4,6-dichloro-3-formyl-1-[N-tert-butoxycarbonyl]-1H-indole-2-carboxylic acid tert butyl ester (0.2 g) in dry tetrahydrofuran (10 ml) was added. The solution was maintained at –20° for 30 min, then warmed up to 25° for 2 hrs. The solution was diluted with hydrochloric acid (50 ml), extracted with ethyl acetate (2×50 ml) and the collected organic phase and concentrated in vacuo. The crude compound was purified by silica gel column chromatography using ethyl acetate/cyclohexane (2/8) as eluant to give the title compound (0.06 g) as a foam. T.l.c. EA/CH (1/1), $R_f$=0.85.

1H—NMR (CDCl$_3$): 1.38(s, 9H), 1.53(s, 9H), 1.64(s, 9H), 4.67(d, 2H), 6.19(ddd, 1H), 6.78(1H), 7.18(d, 1H), 7.58 (ddd, 1H), 7.70(t, 1H), 7.98(d, 1H), 8.23(bm, 1H)

Intermediate 43

1-naphthyl hydrazine

Sodium nitrite (4.8 g) in water (20 ml) was added over 15 minutes to a stirred ice-cold suspension of 1-naphthylamine (9.58 g) in 6 M hydrochloric acid (80 ml). After an additional 30 minutes in the ice bath,, stannous chloride (44.5 g) in 6 M hydrochloric acid (80 ml) was added slowly and the resulting suspension was stirred at 0° for 3 hr. The resulting solid was filtered off and dissolved in a mixture of 40% potassium hydroxide solution (100 ml) and ethyl acetate (150 ml). The organic layer was separated and the aqueous layer was extracted with ethyl acetate (3×100 ml). The combined organic extracts were dried and concentrated under reduced pressure to afford the title compound as a purple solid (10.58 g $R_f$=0.1 in EA/CH (1/4)). I.R. (cm–1) :3312–3474(NH and NH$_2$); 1580–1610,(C=C)

Intermediate 44

1-tert-butoxycarbonyl-2(1-naphthyl) hydrazine

Di tert-butyl dicarbonate (14.3 g) was added to a solution of intermediate 43 (6.9 g) in tetrahydrofuran (350 ml). The solution was stirred at 25° for 8 hrs then concentrated in vacuo affording the crude title compound which was purified by column chromatography (ethylacetate/cyclohexane, 1/4), to give the title compound a brown solid (9 g) T.l.c. EA/CH (1/4) $R_f$=0.45; m.p.=109°

Intermediate 45

1-tert-butoxycarbonyl-2-naphthyl)-pyrazolidin-3-one

To a solution of intermediate 44 (3 g) in dry dimethylformamide (45 ml) was added potassium carbonate (2.2 g) and after 5 min. chloro propionyl chloride (1.5 ml). The resulting mixture was stirred at 25° for 2 hrs, then diluted with diethyl ether (200 ml), washed with water (2×100 ml), dried and concentrated in vacuo. The residue was crystallized from diethyl ether to give a white solid (1.5 g). This was dissolved in dimethylformamide (17.9 ml) and potassium carbonate (0.62 g) was added. The reaction mixture was stirred at 25° for 3 hrs then diluted with diethyl ether (100 ml), washed with water (100 ml), dried and concentrated in vacuo to give a product which was purified by silica gel column chromatography using diethyl ether/cyclohexane (2/1) as eluant to obtain the title compound (1.09 g) as a pale yellow foam. T.l.c. diethyl ether/cyclohexane 2/1); $R_f$=0.37.

Intermediate 46 tert-butyl adamantylidenecarbazate

A hexane solution containing 2-adamantanone (2 g) and tert-butyl carbazate (1.76 g) was heated to reflux for 3 hours. When the solution cooled, the title compound crystallized and was filtered (3.28 g). M.p. 175–177°

Intermediate 47

1-tert-butoxycarbonyl-2-(-2-adamantyl)hydrazine

A solution of intermediate 46 (2.13 g), Pd/C 20% w/w catalyst (0.4 g) and 150 ml of absolute ethanol was placed in a pressure bottle on a Paar hydrogenation apparatus.

Hydrogen uptake at 3 atm (average) continued for 12 hours. The solution was then filtered on celite and the solvent removed under reduced pressure giving the title compound as a solid, m.p. 90–92°.

1H—NMR (CDCl3): 5.29 (bs, 1H), 3.84 (bs, 1H), 3.05 (bs, 1H0, 2.0 (m, 2H), 1.9–1.4 (m, 12H), 1.44 (s, 9H).

Intermediate 48

1-tert-butoxycarbonyl-2-(2-adamantyl)pyrazolidin-3-one

To a solution of intermediate 47 (2 g) in dry dimethylformamide (20 ml) was added potassium carbonate (2.07 g) and after 15 min. chloro propionyl chloride (0.72 ml). The resulting mixture was stirred at room temperature for 3 hours then diluted with diethyl ether (100 ml). Then it was washed with water (100 ml), ammonium chloride (sat, 100 ml) and brine (100 ml). After drying the solvent was removed under reduced pressure and the mixture dissolved in dry dimethylformamide (20 ml). After the addition of potassium carbonate the solution was stirred for 3 hours at room temperature. The reaction mixture was then diluted with diethyl ether (100 ml) and washed with water (100 ml), ammonium chloride (sat, 100 ml) and brine (100 ml). After drying the solvent was removed under reduced pressure to give a crude title compound which was purified by silica gel column chromatography using cyclohexane/ethyl acetate (3/1) as eluant to obtain the title compound (1.73 g).

1H—NMR (CDCl3): 4.08 (m, 1H), 3.91 (m, 2H), 2.6 (m, 2H), 2.52 (t, 2H), 1.9–1.4 (m, 12H), 1.48 (s, 9H).

Intermediate 49

4,6-dichloro-3-[(5-oxo-2-(2-adamantyl)-1-tert-butoxycarbonyl-pyrazolidin-4yl)-hydroxymethyl]1tert-butoxycarbonyl-1H-indole-2-carboxylic acid-tert-butyl ester To a solution of intermediate 48 (0.386 g) in dry tetrahydrofuran (20 ml) was added dropwise and at −78° C. a solution of lithium bis(trimethylsilyl)amide 1 M in tetrahydrofuran (1.44 ml). The reaction mixture was allowed to warm up to −20° in 30 min., then a solution of intermediate 14 (0.2 g) in dry tetrahydrofuran (10 ml) was added. The solution was maintained at −20° for 30 min. then diluted with hydrochloric acid 0.1 M (50 ml) and extracted with ethyl acetate (2×50 ml). The collected organic phase was dried over sodium sulfate and concentrated in vacuum. The crude compound was purified by silica gel column chromatography using ethyl acetate/cyclohexane (1/9) as eluant to give the title compound (0.26 g) as a foam.

1H—NMR (DMSO): 1.38(s, 9H), 1.50(s, 9H), 1.63(d, 9H), 1.6–1.8(m, 14H), 3.2–3.4(bs, 2H), 3.85(dt, 1H), 3.97(s, 1H), 5.61(bs, 1H), 5.78(d, 1H), 7.53 (d, 1H), 7.90(d, 1H).

EXAMPLE 1

Methyl (E)-4,6-dichloro-3-(2-oxo-1-phenyl-pyrrolidin-3-ylidenemethyl)-1H-indole-2carboxylate Intermediate 4 (700 mg) was suspended in ethanol (95%) (10 ml), hydrochloric acid (10 ml, 6 M) was added and the heterogeneous mixture refluxed for 10 h. The suspension was cooled to room temperature and the solid filtered, washed with further portions of 6 M hydrochloric acid and finally vacuum dried to yield the title compound (427 mg) as a white solid IR (nujol) Vmax (cm-1) 1691(C=O), 1672 (C=O).
1N—NMR (DMSO) 12.58 (bs), 7.81(d), 7.71 (t), 7.49 (d), 7.42 (t), 7.29 (d), 7.18 (t), 3.90 (s), 3.88 (t), 3.53 (t), 2.64 (dt).

EXAMPLE 2

(E)-4,6-dichloro-3-(2-oxo-1-phenyl-pyrrolidin-3-ylidenemethyl)-1H-indole-2-carboxylic acid Example 1(136 mg) and lithium hydroxide monohydrate (54 mg) were dissolved in ethanol (95%) (5 ml) and the resulting solution refluxed for 1.5 h. The solvent was evaporated and the residue treated at 50° with 6 M hydrochloric acid for 30 min, then at room temperature for further 30 min. The resulting white solid was filtered, washed and vacuum dried to yield the title compound (110 mg) as a white solid.

IR (nujol) Vmax (cm-1) 3281(C=O), 1630 (C=C).
$^1$H NMR—(DMSO) 13.9–13.3(bs), 12.44 (s), 7.81 (d), 7.72 (t), 7.47 (d), 7.42 (t), 7.26 (d), 7.18 (tt), 3.90 (s), 3.88 (t), 3.53 (t), 2.67 (td).

EXAMPLE 3

(E)-4,6-dichloro-3-(2-oxo-1-phenyl-pyrrolidin-3-ylidenemethyl)-1H-indole-2-carboxylic acid sodium salt Example 2 (100 mg) was suspended at room temperature in sodium hydroxide solution (2,4 ml, 0.1 N) and the mixture was stirred until it became only slightly cloudy (approx 1 h). It was then lyophilized for 48 h to give the title compound (105 mg) as a white solid.

IR (nujol) Vmax (cm-1) 3302 (N—H), 1672 (C=O), 1639 (C=C). $^1$H NMR (DMSO) 12.0–11.0 (bs), 7.82 (t), 7.78 (d), 7.38 (t), 7.35 (d), 7.12 (t), 7.04 (d), 3.79 (t), 2.77 (td).

EXAMPLE 4

Methyl (E)-4,6-dichloro-3-(2-oxo-1-phenyl-piperidin-3-ylidenemethyl)-1H-indole-2-carboxylate Intermediate 5 (680 mg) was suspended in ethanol (95%) (10 ml), hydrochloric acid (10 ml, 6 M) was added and the heterogeneous mixture refluxed for 10 h. The suspension was then cooled to room temperature and the solid filtered, washed with further portions of 6 M hydrochloric acid and finally vacuum dried to yield the title compound (490 mg) as a white solid.

IR (nujol) Vmax (cm-1) 3285 (N—H), 1682 (C=O), 1661 (C=O). $^1$H NMR (DMSO) 12.50 (bs), 7.88 (t), 7.45 (d), 7.40 (m), 7.24 (d), 724 (m), 3.87 (s), 3.71 (t), 2.37 (td), 1.84 (m).

EXAMPLE 5

(E)-4,6-dichloro-3-(2-oxo-1-piperidin-3-ylidenemethyl)-1H-indole-2-carboxylic acid Example 4 (490 mg) and lithium hydroxide monohydrate (200 mg) were dissolved in ethanol (95%) (20 ml) and the resulting solution refluxed for 1.5 h. The solvent was evaporated and the residue treated at 50° with 6 M hydrochloric acid for 30 min, then at room temperature for further 30 min. The resulting white solid was filtered, washed and vacuum dried to yield the title compound (400 mg) as a white solid.

IR (nujol) Vmax (cm-1) 3294 (N—H), 1670 (C=O), 1645 (C=O).
$^1$H NMR (DMSO) 13.43 (bs), 12.36 (bs), 7.89 (t), 7.43 (d), 7.37 (m), 7.24 (m), 7.21 (d), 3.71 (t), 2.39 (td), 1.85 (m).

EXAMPLE 6

(E)-4,6-dichloro-3-(2-oxo-1-phenyl-piperidin-3-ylidenemethyl)-1H-indole-2-carboxylic acid sodium salt Example 5 (100 mg) was suspended at room temperature in sodium hydroxide solution (2.4 ml, 0.1 N) and the mixture was stirred until it became only slightly cloudy (approx 1 h). It was then lyophilized for 48 h to give the title compound (105 mg) as a white solid.

IR (nujol) Vmax (cm-1) 3305 (N—H), 1670 (C=O), 1645 (C=O). $^1$ H NMR (DMSO) 11.6 (bs), 8.00 (t), 7.38 (m), 7.34 (d), 7.22 (tt), 7.03 (d), 3.68 (t), 2.46 (td), 1.81 (m).

EXAMPLE 7

(E)-[(1-tert-butoxycarbonyl-3-oxo-2-phenyl)pyrazolidin-4-ylidene methyl]-4,6-dichloro-1H-indole-2-carboxylic acid To a solution of intermediate 7 (1.6 g) in dry tetrahydrofuran (90 ml) was added dropwise and at −78° a solution of lithium bis(trimethylsilyl)amide 1 M in tetrahydrofuran (6.7 ml). The reaction mixture was allowed to warm up to −20° in 30 min., then a solution of intermediate 8 (2 g) in dry tetrahydrofuran (60 ml) was added. The solution was maintained at −20° for 30 min. then warmed up to 25° for 4 hrs. The solution was diluted with diethyl ether (300 ml) and washed with 0.1 M hydrochloric acid (200 ml). The aqueous solution was extracted with diethyl ether (100 ml) and the collected organic phase was dried and concentrated in vacuum. The crude compound was crystallized from ethyl acetate/n-hexane to give the title compound (0.92 g). m.p.= 182° 1719, 1688 (C=O), 1659. ms (m/z): 502.

EXAMPLE 8

(E)4,6-dichloro-3-(5-oxo-1-phenyl-pyrazolidin-4-ylidenemethyl)-1H-indole-2-carboxylic acid sodium salt The compound of example 7 (0.255 g) was dissolved in dry dichloromethane (5 ml) and trifluoroacetic acid (5 ml). The resulting solution was stirred at 25° for 1 hr then concentrated in vacuo. Trituration of the residue with diethyl ether gave the corresponding acid intermediate (0.177 g). This product (0.155 g) was suspended in water and sodium hydroxide 0.1 M was added (3.77 ml). The heterogeneous solution was stirred at 25° for 2 hrs then freeze-dried to obtain the title compound (0.160 g)

1H-NMR (DMSO); 3.94(d, 2H), 6.26 (t, 1H), 7.08(m+s, 2H), 7.37 (m+s, 3H), 7.83 (bs, 1H), 7.91 (m, 2H), I.R. (cm−1)=3177 (NH), 1674(C=O), 1595(C=C), ms (m/z): 494, 402.

EXAMPLE 9

(E)3-[(1-tert-butoxycarbonyl-2-[(4-tert-butoxycarbonylamino)phenyl]-3-oxo) pyrazolidin-4-ylidene methyl]-4,6-dichloro-1H-indole-2-carboxylic acid To a solution of intermediate 12 (0.47 g) in dry tetrahydrofuran (15 ml) was added dropwise, at −78° a solution of lithium bis(trimethylsilyl)amide 1 M in tetrahydrofuran (2.6 ml). The reaction mixture was allowed to warm up to 20° in 30 min., then a solution of 4,6-dichloro-3-formyl-1-[N-tert-butoxycarbonyl]-1H-indole-2-carboxylic acid ethyl ester (0.436 g) in dry tetrahydrofuran (10 ml) was added. The solution was maintained at −20° for 30 min. then warmed up to 25° for 4 hrs. The solution was diluted with diethyl ether (200 ml) and washed with hydrochloric acid 0.1 M (100 ml). The aqueous solution was extracted with diethyl ether (100 ml) and the combined organic phase was dried and concentrated in vacuo. The crude compound was crystallized from ethyl acetate/n-hexane (1/2) to give the title compound (0.30 g). mp.=220° dec.

I.R. (cm−1): 3418–3281 (NH, OH), 1736, 11713 (C=O) 1676, 1612 (C=C). ms (m/z): 505, 415, 242.

EXAMPLE 10

(E)-4,6-dichloro-3-[(5-oxo-1-(4-aminophenyl))pyrazolidin-4-ylidenemethyl]-1H-indole-2-carboxylic acid hydrochloride salt The compound of example 9 (0.830 g) was dissolved in methanol (60 ml) and hydrogen chloride was bubbled through the solution for 5 min. The resulting solution was stirred at 25° for 2 hrs then concentrated in vacuo. Trituration of the residue with diethyl ether gave the title compound (0.450 g)

1H—NMR (DMSO): 3.86(d, 2H), 7.28(d, 1H), 7.38 (d, 2H), 7.47 (d, 1H), 7.74(t, 1H), 8.00(d, 2H). 10.0 (b, 3H), 12.5(bs, 1H) I.R. (cm−1)=3439–3325(NH), 1730–1676(C=O), 1612(C=C). ms (m/z): 417.

EXAMPLE 11

(E)4,6-dichloro-3-[(5-oxo-1-(4-aminophenyl)pyrazolidin-4-ylidenemethyl]-1H- indole-2-carboxylic acid sodium salt Example 9 (0.200 g) was dissolved in dry dichloromethane (20 ml) and trifluoroacetic acid (6 ml). The resulting solution was stirred at 25° for 2 hrs then concentrated in vacuo. The residue was suspended in water (5 ml), 1 M sodium hydroxide (1 ml) was added and after 5 minutes the solution was acidified with 1 M hydrochloric acid until pH=3. Ethyl acetate (3×100 ml) was added and the organic layers were collected and dried. The solvent was evaporated by distillation under reduced pressure. Trituration of the residue with diethyl ether gave the corresponding acid intermediate (0.060 g). This product (0.019 g) was suspended in water and 0.1 M sodium hydroxide was added (0.45 ml). The homogeneous solution was stirred at 5° for 30 minutes then freeze-dried to obtain the title compound (0.017 g).

1H—NMR (DMSO): 3.82(d, 2H), 6.56(d, 2H), 7.21(d, 1H), 7.42(d, 1H), 7.54(d+s, 2H+1H), 11.5–13.0(bm, 1H). I.R. (cm−1)=3440–2680(NH), 1734(C=O), 1587(C=C).

EXAMPLE 12

(Z)4,6-Dichloro-3-(2,5-dioxo-1-phenyl-imidazolidin-4-ylidenemethyl)-1H-indole-2-carboxylic acid Intermediate 16 (140 mg) was suspended in formic acid (10 ml) and stirred at room temperature for 10 hs. The solvent was removed under reduced pressure to give the title compound as a cream solid (92 mg, mp.>250°).

IR (Nujol) $v_{max}$(cm−1) 3186 (N—H), 1769 (C=O), 1732 (C=C) and 1691 (C=O). $^1$H—NMR (DMSO) 12.42 (bs), 10.70 (bs), 7.49 (td), 7.44 (d), 7.43 (d), 7.40 (tt), 7.25 (d) and 7.04 (s).

EXAMPLE 13

(E)4,6-Dichloro-3-(2,5-dioxo-1-phenyl-imidazolidin-4-ylidenemethyl)-1H-indole-2-carboxylic acid allyl ester Intermediate 19 (360 mg) was suspended in formic acid (20 ml) and stirred at room temperature for 5 h. The solvent was removed under reduced pressure to give the title compound as a yellow solid (296 mg, mp.>250°).

IR (Nujol) $v_{max}$(cm−1) 3261 (N—H), 1757 (C=O), 1720 (C=C) and 1668 (C=C). $^1$H—NMR (DMSO) 12.47 (bs), 10.98 (bs), 7.45 (td), 7.44 (d), 7.35 (tt0, 7.28 (dd), 7.22 (d), 6.82 (s), 5.94 (m), 5.35 (m) and 4.76 (d).

EXAMPLE 14

(E)4,6-Dichloro-3-(2,5-dioxo-1-phenyl-imidazolidin-4-ylidenemethyl)-1H-indole-2-carboxylic acid To a solution of example 13 (290 mg) in dry THF (10 ml) 5,5-dimethyl-1,3-cyclohexandione (98 mg) and palladium tetrakis triphenylphosphine (18.4 mg) were added. The mixture was stirred at room temperature for 2 hs then diluted with ethyl acetate and quenched with water. The solvent was removed under reduced pressure, the precipitate dissolved in diethyl ether and extracted with a solution of $Na_2CO_3$ (5%). The aqueous solution was acidified giving a precipitate which was collected by filtration to furnish the title compound as a yellow solid (147 mg mp.>250°).

IR (Nujol) $v_{max}$(cm−1) 3335 (N—H), 1763–1724 (C=O) and 1678–1664 (C=O). $^1$H—NMR (DMSO) 12.35 (bs), 10.95 (bs), 7.50–7.28 (m), 7.20 (d) and 6.83 (s).

EXAMPLE 15

(E)3-[(1-tert-butoxycarbonyl-3-oxo-2-phenyl)pyrazolidin-4-ylidene methyl]-4,6-dichloro-1H-indole-2-carboxylic acid tert-butyl ester A suspension of example 7 (0.7 g) in benzene was heated at reflux and then N,Ndimethylformamide-di-tert-butyl acetal (1.5 ml) was added dropwise. The resultant solution was heated at reflux for 30 min. then diluted with ethyl acetate (100 ml), washed with sodium bicarbonate (sat.) (100 ml), brine (100 ml), dried and concentrated in vacuo to afford the crude title compound (0.7 g), T.l.c. EA/CH (6/24), $R_f$=0.8.
1H—NRM (CDCl$_3$): 1.23 (s, 9H), 1.57(s, 9H), 4.60(d, 2H), 7.14(m, 1H), 7.18(d, 1H), 7.35(d, 1H), 7.40(m, 2H), 7.70(m, 2H), 7.93(t, 1H), 9.15(bs, 1H).

EXAMPLE 16
3-[2-(4-amino-phenyl)-1-tert-butoxycarbonyl-3-oxo-pyrazolidin-4-ylidenemethyl]-4,6-dichloro-1H-indole-2-carboxylic acid Example 9 (0.110 g) was dissolved in dry dichloromethane (11 ml) and trifluoroacetic acid (0.55 ml). The resulting solution was stirred at 0° for 3 hrs then concentrated in vacuo. Trituration of the residue with diethyl ether (6 ml) gave the corresponding title compound as a brown solid (0.070 g).
1H—NMR (DMSO): 1.22(s,9H), 4.50(d,2H), 7.30(d, 1H), 7.43(d,2H), 7.48(d,1H), 7.76(t,1H),12.6(s,1H).

EXAMPLE 17
3-[2-(4-Acetylamino)-phenyl)-1-tert-butoxycarbonyl-3-oxo-pyrazolidin-4-ylidenemethyl]-4,6-dichloro-1H-indole-2-carboxylic acid To a solution of example 16 (0.200 gr) in dry tetrahydrofuran (5 ml) under nitrogen was added trimethylamine (0.115 ml). After 5 minutes at 0°, chloroacetyl chloride (0.040 ml) was added dropwise to the stirred solution. The reaction mixture was allowed to warm up to room temperature over 2 hrs and then a solution of 5% sodium bicarbonate (30 ml) was added. The reaction mixture was extracted with ethyl acetate (3×20) and the combined organic phases dried and concentrated in vacuo. The crude title compound was purified by silica gel flash column chromatography (dichloromethane:methanol:acetic acid=90:5:5) to gives the title compound a yellow solid (0.023 g).
I.R. (cm-1, Nujol):3500–2500 (OH,NH), 1668(C=O), 1607(C=O, C=C).

EXAMPLE 18
4,6-Dichloro-3-[5-oxo-1-(4-acetylamino-phenyl)-pyrazolidin-4-ylidenemethyl]-1H-indole-2-carboxylic acid Example 17 (0.023 g) was dissolved in dry dichloromethane (5 ml) and trifluoroacetic acid (5 ml). The resulting solution was stirred at 25° for 2 hrs then concentrated in vacuo. Trituration with diethyl ether (5 ml) afforded title compound as a pale brown solid (0.030 g)
1H—NMR (DMSO): 2.02(s,3H), 3.83(m,2H), 6.40(s,1H), 7.26(d,1H), 7.45(d,1H), 7.58(m,2H), 7.67(t,1H), 7.82(m, 2H),9.95(s, 1H), 12.44(s,1H), 13.7(s,1H).
I.R. (cm-1, Nujol):3500–2500 (OH—NH), 1678–1650 (C=O), 1601(C=C).

EXAMPLE 19
3-[1-tert-butoxycarbonyl-3-oxo-2-(4-ureido-phenyl)-pyrazolidin-4-ylidenemethyl]-4,6-dichloro-1H-indole-2-carboxylic acid To a solution of example 16 (0.070 g) in tetrahydrofuran (4 ml) under nitrogen at room temperature was added trimethylsilylisocyanate (0.080 ml). The solution was refluxed for 4 hrs, after which time the product was seen to precipitate from the solution. The solid was filtered off and washed with tetrahydrofuran (10 ml) affording the title compound as an orange solid. (0.042 g).
1H—NMR (DMSO): 1.22(s,9H), 4.52(m,2H), 5.87(s,2H), 7.30(s,1H), 7.45(m,4H), 7.50(m,1H), 7.80(s,1H), 8.65(s, 1H), 12.5(s,1H).
I.R. (cm-1,Nujol): 3489–3341(NH).

EXAMPLE 20
4,6-Dichloro-3-[5-oxo-1-(4-ureido-phenyl)-pyrazolidin-4-ylidenemethyl]-1H-indole-2-carboxylic acid Example 19 was dissolved in dry dichloromethane (10 ml) ad trifluoroacetic acid (2 ml). The resulting solution was stirred at 25° for 2 hrs then concentrated in vacuo. Trituration with diethyl ether (5 ml) afforded the title compound as a red solid (0.030 g).
1H—NMR (DMSO):3.81(m,2H), 5.82(s,2H), 6.36(s,1H), 7.25(d,1H), 7.39–7.45(m,3H), 7.65(t,1H), 7.75(m,2H), 8.53 (s,1H), 12.43(s,1H), 13.71(s,1H).
I.R. (cm-1, Nujol):3500–2600(OH,NH).

EXAMPLE 21
3-[1-tert-butoxycarbonyl-2-[4-methylsulfamidophenyl)-3-oxo-pyrazolidin-4-ylidenemethyl]-4,6-dichloro-1H-indole-2-carboxylic acid To a solution of intermediate 23 (0.100 g) in dry tetrahydrofuran (5 ml) was added dropwise, at −78°, a 1 M solution of lithium bis(trimethylsilyl)amide in tetrahydrofuran (0.53 ml). The reaction mixture was allowed to warm up to 20° over 30 min., then a solution of 4,6-dichloro-3-formyl-1-[N-tertbutoxycarbonyl]-1H-indole-2-carboxylic acid ethyl ester (0.100 g) in dry tetrahydrofuran (4 ml) was added. The solution was maintained at −20° for 30 min. then warmed up to 25° over 4 hrs. The solution was diluted with diethyl ether (20 ml) and washed with 0.1 M hydrochloric acid (10 ml). The aqueous solution was extracted with diethyl ether (15 ml) and the combined organic phases were dried and concentrated in vacuo. The crude compound was purified by silica gel flash column chromatography (dichloromethane:methanol:acetic acid=90:5:5) to the title compound (0.035 g).

EXAMPLE 22
4,6-Dichloro-3-[1-(4-methylsulfamidophenyl)-5-oxo-pyrazolidin-4-ylidenemethyl]-1H-indole2-carboxylic acid Example 21 (0.035 g) was dissolved in dry dichloromethane (6 ml) and trifluoroacetic acid (2 ml). The resulting solution was stirred at 25° for 2 hrs then concentrated in vacuo. Trituration with ethyl acetate (5 ml) afforded the title compound as a yellow solid (0.010 g).
1H—NMR (DMSO):2.94(s,3H), 3.83(bm, 2H), 6.40(bs, 1H), 7.22(d,2H), 7.26(d,1H), 7.45(d,1H), 7.68(t,1H), 7.86 (d,2H),9.67(s,1H), 12.48(bs,1H).
I.R. (cm-1, Nujol):3186 (NH), 1680(C=O), 1640(C=O, C=C).

EXAMPLE 23
(E)-3[(2-methyl-5-oxo-1-phenyl)pyrazolidin-4-ylidene methyl]-4,6-dichloro-1H-indole-2-carboxylic acid To a solution of intermediate 25 (0.365 g) in dry tetrahydrofuran (10 ml) was added dropwise and at −78° a solution of lithium bis(trimethylsilyl)amide 1 M in tetrahydrofuran (1.33 ml). The reaction mixture was allowed to warm up to −20° in 30 min., then a solution of intermediate 8 (0.2 g) in dry tetrahydrofuran (10 ml) was added. The solution was diluted with diethyl ether (300 ml) and washed with hydrochloric acid 0.1 M (200 ml). The aqueous solution was extracted with diethyl ether (100 ml) and the collected organic phase was dried and concentrated in vacuo. The crude compound was triturated with diethyl ether to give the title compound (0.06 g).
1H—NMR (DMSO): 3.31(s, 3H), 3.63(bs, 1H), 4.08(bs, 1H), 7.16(t, 1H), 7.27(d, 1H), 7.42 (t, 2H), 7.45(d, 1H), 7.83(s, 1H), 7.84(d,2H), 12.48(s,1H), 13.75(bs, 1H).
I.R. (cm-1): 3244(NH), 1676(C=O), 1653(C=C).

EXAMPLE 24
4,6-dichloro-3-(3-oxo-2-phenyl-isoxazolidin-4-ylidene methyl)-1H-indole-2-carboxylic acid To a solution of intermediate 27 (0.475 g) in dry tetrahydrofuran (20 ml) was added dropwise and at −78° C. a solution of lithium bis(trimethylsilyl)amide 1 M in tetrahydrofuran (3.2 ml). The reaction mixture was allowed to warm up to −20° in 30 min., then a solution of ethyl 4,6 dichloro-3-formyl-1-1-butoxycarbonyl 1Hindole-2-carboxylate (0.94 g) in dry tetrahydrofuran (20 ml) was added. The solution was maintained at −20° for 30 min. then warmed up to 25° for 4 hrs. The solution was diluted with diethyl ether (300 ml) and washed with hydrochloric acid 0.1 M (200 ml). The aqueous solution was extracted with diethyl ether (100 ml) and the collected organic phase was dried and concentrated in vacuum. The crude compound was purified by silica gel column chromatography using ethyl acetate/cyclohexane as eluant to give the crude title compound (0.16 g) with T.l.c. dichloromethane/methanol 27/3, $R_f$=0.3.

EXAMPLE 25
4,6-Dichloro-3-(3-oxo-2-phenyl-isoxazolidin-4-ylidene methyl)-1H-indole-2-carboxylic acid tert butyl ester The product of Example 24 was treated with N,Ndimethylformamide-di-tert--butyl acetal (0.44 ml) in benzene (15 ml). The resultant solution was heated at reflux for 30 min. then concentrated in vacuo to afford the crude compound that was purified by silica gel column chromatography using ethyl acetate/cyclohexane as eluant to give the title compound (0.03 g). T.l.c. ethyl acetate/cyclohexane (1/2), $R_f$=0.6. m.p.=120° C.
1H—NMR (CDCl$_3$): 1.59(s, 9H), 5.04(d, 2H), 7.17(t, 1H), 7.18(d,1H), 7.34(d, 1H), 7.40(t,2H), 7.85(d, 2H), 7.91(t, 1H), 9.05(bs, 1H).

EXAMPLE 26
4,6-Dichloro-3-(3-oxo-2-phenyl-isoxazolidin-4-ylidene-methyl)-1H-indole-2-carboxylic acid Example 25 (0.025 g) was dissolved in dry dichloromethane (3 ml) and trifluoroacetic acid (2 ml). The resulting solution was stirred at 25° for 1 hr then concentrated in vacuo. Trituration with isopropanol of the residue gave the title compound as a solid (0.014 g). m.p.>250°.
1H—NMR (DMSO): 5.07(d, 2H), 7.20(t, 1H), 7.30(d, 1H), 7.45(t, 2H), 7.47(d, 1H), 7.74(dd, 2H), 7.85(t, 1H), 12.59(s, 1H), 13.89(bs, 1H).
I.R. (cm−1): 3304(NH), 1672(C=O), 1645(C=C). ms (m/z): 403.

EXAMPLE 27
(E) 4,6-dichloro-3-[(5-oxo-1-(3-aminophenyl)pyrazolidin-4-ylidenemethyl]-1H-indole-2-carboxylic acid hydrochloride salt To a solution of intermediate 30 (0.03 g) and intermediate 31 (0.03 g) in methanol (30 ml) was bubbled hydrogen chloride at 0° for 5 min. The resulting solution was stirred at 25° for 1 hrs then concentrated in vacuo. Trituration of the residue with diethyl ether gave the title compound (0.01 g).
1H—NMR (DMSO): 5.85(d, 2H), 7.08(d, 1H), 7.27(d, 1H), 7.47(d, 1H), 7.48(t, 1H), 7.76(t, 1H), 7.83(d, 1H), 8.02(s, 1H), 9.5–10.5(b, 3H), 12.5(bs, 1H).
I.R. (cm−1): 3400–3200(NH and OH), 1711(C=O).

EXAMPLE 28
(E) 4,6-dichloro-3-(2,5-dioxo-1-phenyl-pyrrolidin-3-ylidenemethyl)-1H-indole-2-carboxylic acid A suspension of intermediate 32 (295 mg) in formic acid (40 ml) was stirred at room temperature for 6 hours the the solvent removed under reduced pressure. The residue was triturated with ethyl acetate and filtered to give the title compound as cream solid (148 mg, mp.>250°).
IR (Nujol)$v_{max}$(cm−1) 3204(N—H), 1705(C=O).
1H—NMR (DMSO) 14—(bs), 12.6(s), 8.08(t), 7.51(tt), 7.475(d), 7.43(m), 7.38(d), 7.30(d), 3.38(d).

EXAMPLE 29
(E) 3-[(1-tert-butoxycarbonyl-3-oxo-2-phenyl)-tetrahydro-pyridazine-4-ylidenemethyl]-4,6-dichloro-1H-indole-2-carboxylic acid To a solution of intermediate 33 (0.85 g) in dry tetrahydrofuran (8 ml) was added dropwise and a −50° a solution of lithium bis(trimethylsilyl)amide 1 M in tetrahydrofuran (2 ml) and the reaction mixture was stirred at −20/−40° for 30 min. Then the solution was cooled at −60° and a solution of intermediate 8 (0.3 g) in dry tetrahydrofuran (7 ml) was added. The solution was warmed up to 25° and stirred for 3 hrs then it was diluted with ethyl acetate (300 ml) and washed with hydrochloric acid (2 M (20 ml) and brine (2×30 ml). The collected organic phase was dried and concentrated in vacuum. The crude compound was crystallized from ethyl acetate/n-hexane (5 ml/8 ml) at 0° C. to give the title compound (0.2 g). mp.>240°.
1H—NMR (DMSO): 1.28(s, 9H), 2.56(bs, 2H), 3.84(bs, 2H), 7.19(tt, 1H), 7.19(d, 1H), 7.37(t, 2H), 7.46(d, 1H), 7.60(dd, 2H), 8.0(t, 1H), 12.8(bs, 1H), 13.5(bs, 1H).

EXAMPLE 30
(E) 4,6-dichloro-3-(3-oxo-2-phenyl-tetrahydro-pyridazine-4-ylidenemethyl)-1H-indole -2-carboxylic acid To a solution of example 29 (0.117 g) in dichloromethane (10 ml) was added dropwise trifluoroacetic acid (3 ml) at 0° C. The reaction mixture was warmed up to 25° and stirred for 2 hr then concentrated in vacuo. The residue was dissolved in ethyl acetate (30 ml), basified with a 5% solution of sodium hydrogen carbonate and acidified with a saturated solution of ammonium chloride. The organic phase was dried and concentrated in vacuo. The residue was triturated in ethyl acetate/diethyl ether (2 ml/1 ml) to give the title compound (0.046 g) as a pale yellow powder mp.>250°.
1H—NMR (DMSO): 3.10(m, 2H),3.35(m, 2H), 6.02(t,1H), 7.12(t,1H), 7.12(t,1H), 7.22(d,1H), 7.33(t, 2H), 7.43(d, 1H), 7.63(d, 2H), 8.00(t, 1H), 12.36(s, 1H), 13.50(bs, 1H).

EXAMPLE 31
(E) 4,6-dichloro-3-[(5-oxo-1-(2-quinolinyl)pyrazolidin-4-ylidenemethyl]-1H-indole-2-carboxylic acic hydrochloride salt To a solution of intermediate 38 (0.115 g) in methanol (15 ml) was bubbled hydrogen chloride at 25° for 5 min. The resulting solution was stirred at 25° for 4 hrs then concentrated in vacuo. Trituration of the residue with diethyl ether gave the title compound (0.035 g). m.p.>240°.

EXAMPLE 32
(E) 4,6-dichloro-3-[(5-oxo-1-(2-pyridyl))pyrazolidin-4-ylidenemethyl]-1H-indole-2-carboxylic acid hydrochloride salt To a solution of intermediate 42 (0.055 g) in methanol (15 ml) was bubbled hydrogen chloride at 25° for 5 min. The resulting solution was stirred at 25° for 6 hrs then concentrated in vacuo. Trituration of the residue with diethyl ether gave the title compound (0.02 g). m.p.>240°.

EXAMPLE 33
(E)3-[1-tert-butoxycarbonyl-2-(1-naphthyl)-3-oxo] pyrazolidin-4-ylidene methyl]-4,6-dichloro-1-tert-butoxycarbonyl-1H-indole-2-carboxylic acid tert butyl ester To a solution of intermediate 45 (0.18 g) in dry tetrahydrofuran (10 ml) was added dropwise, at −78° a solution of lithium bis(trimethylsilyl)amide 1 M in tetrahydrofuran (0.58 ml). The reaction mixture was allowed to warm up to −20° in 30 min, then the reaction mixture was cooled at −40° and a solution of 4,6-dichloro-3-formyl-1-[N-tert-butoxycarbonyl]-1H-indole-2-carboxylic acid tert butyl ester (0.2 g) in dry tetrahydrofuran (6 ml) was added. The solution was maintained at −40° for 20 min. then slowly warmed up to 25° for 2 hrs. The solution was poured in a saturated ammonium chloride solution and extracted with ethyl acetate (200 ml). The organic layer was washed with water, dried and concentrated in vacuo. The crude compound was purified by silica gel column chromatography using diethylether/cyclohexane (3/7) as eluant to give the title compound (0.030 g) as a yellow wax, T.l.c. diethylether/cyclohexane (1/2), $R_f$=0.55
I.R. (cm-1)=3500–2700(NH), 1720–1690 (C=O;

EXAMPLE 34

(E) 4,6-dichloro-3-(5-oxo-1(1-naphthyl)-pyrazolidin-4-ylidenemethyl)-1H-indole-2carboxylic acid
Example 33 (0.030 g) was dissolved in dry dichloromethane (5 ml) and trifluoroacetic acid (4 ml). The resulting solution was stirred at 25° for 1 hr then concentrated in vacuo. Trituration of the residue with diethyl ether gave the title compound (0.010 g), m.p.200° dec.
$^1$H—NMR (DMSO): 14.2–12.5(broad, 1H), 12.46 (s, 1H), 8.04, 7.90 (m, 3H), 7.76 (t, 1H), 7.66–7.56 (m, 4H), 7.50 (d, 1H), 7.30 (d, 1H), 6.60 (s, 1H), 4.04 (d, 2H);
I.R. (cm−1)=3410–3184 (OH,NH), 1707–1686(C=O), 1659(C=C).

EXAMPLE 35

(E)3-[(1-tert-butoxycarbonyl-3-oxo-2-(2-adamantyl)) pyrazolidin-4-ylidene methyl]-4,6-dichloro-1H-indole-2-carboxylic acid-tert-butyl ester
To a solution of intermediate 49 (0.144 g) in tetrahydrofuran (10 ml) was added dropwise and at 0° a solution of lithium bis(trimethylsilyl)amide 1 M in tetrahydrofuran (0.2 ml). The reaction mixture was allowed to warm up to 25° for 2 hrs then diluted with hydrochloric acid 0.1 M (50 ml) and extracted with diethyl ether (2×50 ml). The collected organic phase was dried over sodium sulfate and concentrated in vacuum. The crude compound was purified by silica gel column chromatography using ethyl acetate/cyclohexane (1/9) as eluant to give the title compound (0.02 g) as a foam.
1H—NMR (CDCl3): 0.75–2.00 (m+s+s, 30H ), 2.75(m, 2H), [4.22(bs)–4.34(d)3H], [7.13(d)–7.33(d)–7.69(t), 3H], 9.15(bs, 1H).

EXAMPLE 36

(E) 4,6-dichloro-3-[5-oxo-1-(2-adamantyl)pyrazolidin-4-ylidenemethyl]-1H-indole-2-carboxylic acid
Example 35 (0.02 g) was dissolved in dry dichloromethane (1 ml) and trifluoroacetic acid (1 ml). The resulting solution was stirred at 25° for 1 hr then concentrated in vacuo. Trituration with diethyl ether of the residue gave the title compound (0.003 g), m.p.190° dec.
1H—NMR (DMSO): 150–1.92(m, 10H), 2.20–2.32(m, 4H), 3.67(d, 2H), 4.02(bs, 1H), 5.7(b, 1H), 7.26(d, 1H),[7.46(d)–7.51(t), 2H],12.41(bs, 1H), 13.56(bs, 1H).

EXAMPLE 37

(Z) 4,6-dichloro-3-(5-oxo-1-phenyl-pyrazolidin-4-ylidenemethyl)-1H-indole-2-carboxylic acid
The intermediate 21 (0.125 g) was dissolved in dry dichloromethane (5 ml) and trifluoromethane acid (5 ml). The resulting solution was stirred at 25° for 1 hr then concentrated in vacuo. Trituration with diethyl ether of the residue gave title compound acid (0.041 g).
1H—NMR (DMSO): 4.15(d, 2H), 6.48(bm, 1H), 7.05(m, 1H), 7.14(d, 1H), 7.18(t, 1H), 7.30(t, 2H), 7.41(d, 1H), 7.74(d, 2H), 12.24(s, 1H), 13.31(bs, 1H).

| | |
|---|---|
| Active ingredient | 200.0 mg |
| Starch 1500 | 32.5 mg |
| Microcrystalline Cellulose | 60.0 mg |
| Croscarmellose Sodium | 6.0 mg |
| Magnesium Stearate | 1.5 mg |

The active ingredient is blended with the other excipients. The blend can be used to fill gelatine capsules or compressed to form tablets using appropriate punches. The tablets can be coated using conventional technqiues and coatings.
B. Tablet

| | |
|---|---|
| Active ingredient | 200.0 mg |
| Lactose | 100.0 mg |
| Microcrystalline Cellulose | 28.5 mg |
| Povidone | 25.0 mg |
| Croscarmellose Sodium | 6.0 mg |
| Magnesium Stearate | 1.5 mg |

The active ingredient is blended with lactose, microcrystalline cellulose and part of the croscarmellose sodium. The blend is granulated with povidone after dispersing in a suitable solvent (i.e. water). The granule, after drying and comminution is blended with the remaining excipients. The blend can be compressed using appropriate punches and the tablets coated using conventional techniques and coatings.
C. Injection Formulation

| | |
|---|---|
| Active ingredient | 0.1–7.00 mg/ml |
| Sodium phosphate | 1.0–50.00 mg/ml |
| NaOH qs desidered pH (range 3–10) | |
| water for injection qs to | 1 ml |

The formulation may be packed in glass (ampoules) with a rubber stopper (vials, syringes) and a plastic/metal overseal (vials only).
D. Dry Powder for constitution with a suitable vehicle

| | |
|---|---|
| Active ingredient: | 0.1–100.00 mg |
| Mannitol qs to | 0.02–5.00 mg | packed in glass vials or syringes,with a rubber stopper and (vials only) a plastic metal overseal.
E. Inhalation Cartridges

| | mg/cartidge |
|---|---|
| Active ingredient (micronised) | 5.00 |
| Lactose to | 25.00 |

The active ingredient is micronised in a fluid energy mill to a fine particle size range prior to blending with normal tabletting grade lactose in a high energy mixer. The powder blend is filled into a proper unit dose container as blister or capsule for use in a suitable inhalation or insufflation device.

The affinity of the compound of the invention for strychnine insensitive glycine binding site was determined using the procedure of Kishimoto H. et al J. Neurochem 1981, 37, 1015–1024. The pKi values obtained with representative compounds of the invention are given in the following table.

| Example No. | pKi |
|---|---|
| 3 | 7.29 |
| 6 | 7.31 |
| 8 | 8.0 |
| 10 | 7.83 |
| 12 | 7.43 |
| 14 | 7.13 |
| 18 | 7.7 |
| 20 | 7.69 |
| 22 | 7.66 |
| 23 | 7.46 |
| 26 | 7.12 |
| 27 | 7.7 |
| 28 | 7.38 |
| 34 | 7.31 |

The ability of compounds of the invention to inhibit NMDA induced convulsions in the mouse was determined using the procedure of Chiamulera C et al. Psychopharmacology 1990, 102, 551–552. In this test the ability of the compound to inhibit the generalized seizures induced by an intracerebroventricular injection of NMDA in mice was examined at a number of dose levels. From these results the dose required to protect 50% of the animals from the convulsion action of the NMDA was calculated. This expressed as mg/kg is referred to as the $ED_{50}$ value.

Representative results obtained for compounds of the invention when given by intravenous (IV) and oral (po) administration are given in the following table.

| Ex. No. | $ED_{50}$ i.v | $ED_{50}$ po |
|---|---|---|
| 3 | 0.08 | 3.83 |
| 6 | 0.09 | 7.50 |
| 8 | 0.1 | 1.70 |
| 10 | 0.1 | 1.7 |

The compounds of the invention are essentially non toxic at therapeutically useful doses. Thus for an example the compound of Example 8 showed no adverse affects when administered to anaesthetised cats or conscious dogs at doses up to 24 mg/kg.

What is claimed is:

1. A method of treatment of pain in a mammal which comprises administering to the mammal an effective amount of a compound of formula I

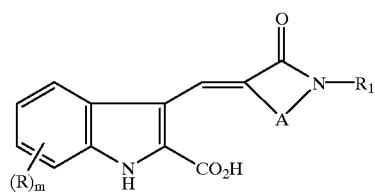

(I)

or a salt, or metabolically labile ester thereof wherein R represents a group selected from halogen, alkyl, alkoxy, amino, alkylamino, dialkylamino, hydroxy, trifluoromethyl, trifluoromethoxy, nitro, cyano, $SO_2R_2$ or $COR_2$ wherein $R_2$ represents hydroxy, methoxy, amino, alkylamino, or dialkylamino, m is zero or an integer 1 or 2;

$R_1$ represents a cycloalkyl, bridged cycloalkyl, heteroaryl, bridged heterocyclic or optionally substituted phenyl or fused bicyclic carbocylic group;

A represents a $C_{1-4}$ alkylene chain or the chain $(CH_2)_pY(CH_2)_q$ wherein Y is O, S(O)n or $NR_3$ and which chains may be substituted by one or two groups selected from $C_{1-6}$ alkyl optionally substituted by hydroxy, amino, alkylamino or dialkylamino, or which chains may be substituted by the group=O;

$R_3$ represents hydrogen, alkyl or a nitrogen protecting group;

n is zero or an integer from 1 or 2;

p is zero or an integer from 1 to 3;

q is zero or an integer from 1 to 3 with the proviso that the sum of p+q is 1, 2 or 3.

2. A method as claimed in claim 1, wherein the compound of formula (I), m is 2 and R is chlorine at the 4 and 6 positions in the indole nucleus.

3. A method as claimed in claim 1 wherein A in the compound of formula (I) is a chain which is o—$(CH_2)_2$—, —$(CH_2)_3$—, —$CH_2CO$—, —$CH_2NH$—, —$CH_2NCH_3$—, —$(CH_2)_2NH$—, —NHCO— or —$CH_2O$—.

4. A method as claimed in claim 1 wherein the compound of formula (I) is (E)4,6-dichloro-3-(5-oxo-1-phenyl-pyrazolidin-4-ylidenemethyl)-1H-indole-2-carboxylic acid and physiologically acceptable salts or metabolically labile esters thereof.

5. A method as claimed in claim 1, wherein the compound of formula (I) is (E)-4,6-dichloro-3-(2-oxo-1-phenyl-pyrrolidin-3-ylidenemethyl)-1-1H-indole-2-carboxylic acid.

6. A method as claimed in claim 1, wherein the compound of formula (I) is (E)-4,6-dichloro-3-(2-oxo-1-phenyl-pyrrolidin-3-ylidenemethyl)-1-1H-indole-2-carboxylic acid sodium salt.

7. A method as claimed in claim 1, wherein the mammal is a man.

8. A method as claimed in claim 2, wherein the mammal is a man.

9. A method as claimed in claim 3, wherein the mammal is a man.

10. A method as claimed in claim 4, wherein the mammal is a man.

11. A method as claimed in claim 5, wherein the mammal is a man.

12. A method as claimed in claim 6, wherein the mammal is a man.

* * * * *